United States Patent
Kobayashi et al.

(10) Patent No.: US 10,585,053 B2
(45) Date of Patent: Mar. 10, 2020

(54) X-RAY DIFFRACTOMETER

(71) Applicant: Rigaku Corporation, Akishima-shi, Tokyo (JP)

(72) Inventors: Shintaro Kobayashi, Akishima (JP); Katsuhiko Inaba, Akishima (JP)

(73) Assignee: RIGAKU CORPORATION, Akishima-Shi, Tokyo (JP)

(*) Notice: Subject to any disclaimer, the term of this patent is extended or adjusted under 35 U.S.C. 154(b) by 271 days.

(21) Appl. No.: 15/622,900

(22) Filed: Jun. 14, 2017

(65) Prior Publication Data
US 2017/0363550 A1     Dec. 21, 2017

(30) Foreign Application Priority Data
Jun. 15, 2016  (JP) ................. 2016-118860

(51) Int. Cl.
| | |
|---|---|
| G01N 23/207 | (2018.01) |
| G01N 23/20008 | (2018.01) |
| G01N 23/201 | (2018.01) |
| G01C 9/00 | (2006.01) |
| G21K 1/02 | (2006.01) |

(52) U.S. Cl.
CPC ............. *G01N 23/207* (2013.01); *G01C 9/00* (2013.01); *G01N 23/201* (2013.01); *G01N 23/20008* (2013.01); *G21K 1/02* (2013.01); *G01N 2223/316* (2013.01); *G01N 2223/61* (2013.01)

(58) Field of Classification Search
CPC .............. G01N 23/207; G01N 23/20; G01N 23/20008; G01N 23/203; G01K 1/06; G01K 1/102
See application file for complete search history.

(56) References Cited

U.S. PATENT DOCUMENTS

2008/0095311 A1* 4/2008 Zheng ................... G01N 23/20
378/71
2013/0136236 A1  5/2013 Morikawa et al.

FOREIGN PATENT DOCUMENTS

| JP | H03-114053 U | 11/1991 |
| JP | H09-281061 A | 10/1997 |
| JP | 11-287773 A | 10/1999 |
| JP | 11-304729 A | 11/1999 |
| JP | 2002-310948 A | 10/2002 |

(Continued)

OTHER PUBLICATIONS

Extended European Search Report dated Sep. 19, 2017, issued by the European Patent Office in corresponding European Application No. 17175435.1. (6 pages).

(Continued)

*Primary Examiner* — Don K Wong
(74) *Attorney, Agent, or Firm* — Buchanan Ingersoll & Rooney PC

(57) ABSTRACT

An X-ray diffractometer for obtaining X-ray diffraction angles of diffracted X-rays by detecting with an X-ray detector diffracted X-rays diffracted at a sample when X-rays are emitted at the sample at each angle of the angles about a center point of goniometer circles, the X-ray diffractometer having a pinhole member provided with a pinhole, the pinhole allowing X-rays diffracted from the sample to pass so that the diffracted X-rays pass through the center point of the goniometer circle, and other diffracted X-rays are shielded by the pinhole member.

7 Claims, 15 Drawing Sheets

(56) References Cited

FOREIGN PATENT DOCUMENTS

JP 2013-108940 A 6/2013

OTHER PUBLICATIONS

Office Action (Notice of Reasons for Refusal) dated Apr. 17, 2019, by the Japanese Patent Office in corresponding Japanese Patent Application No. 2016-118860 and English translation of the Office Action. (9 pages).

* cited by examiner

⟨X-RAY DIFFRACTION DIAGRAM⟩

⟨RECIPROCAL-SPACE MAPPING DIAGRAM⟩

SPREADING OF DIFFRACTED X-RAYS

FIG. 11
HIGH-INTENSITY IS OBTAINED
AND THEREFORE HIGHER ORDER
REFLECTANCE IS OBTAINED

X-RAY DIFFRACTOMETER

BACKGROUND OF THE INVENTION

Field of the Invention

The present invention relates to a parallel-beam X-ray diffractometer in which the X-ray diffractometer uses a parallel-beam optical system.

Description of the Related Art

Conventionally known is an X-ray diffractometer that uses a Bragg-Brentano parafocusing geometry (i.e., a focusing optical system) in which a divergent beam emitted from an X-ray source is used to perform measurement. This X-ray diffractometer is sometimes called a Bragg-Brentano parafocusing X-ray diffractometer. In addition to this Bragg-Brentano parafocusing X-ray diffractometer, a parallelized X-ray beam may be used for the purpose of making the angle of the X-rays incident on the sample uniform in the measurement of a thin film or other sample. An X-ray diffractometer that uses the parallelized X-ray beam, i.e., a parallel-beam X-ray diffractometer is well-known in recent years.

The X-ray source and X-ray detector are disposed on the same goniometer circle in the Bragg-Brentano parafocusing X-ray diffractometer. The X-ray source, sample, and X-ray detector are disposed on a focusing circle. Meanwhile, in a parallel-beam X-ray diffractometer, the X-ray source and X-ray detector are not required to be disposed on the same goniometer circle, and furthermore, the X-ray source, sample, and detector are not required to be disposed on a focusing circle.

Examples of a parallel-beam X-ray diffractometer include an in-plane X-ray diffractometer, an in-plane reciprocal-space mapping apparatus, and a GI-WAXS/SAXS apparatus. These apparatuses are devices such as the following. In the present specification, "diffraction" shall include "scattering."

(In-Plane X-Ray Diffractometer)

In accordance with X-ray diffraction, the structure of various substances on an atomic level can be investigated. Furthermore, in recent years, there is a need for investigating the structure of a thin film on a nanometer size scale. Measurement that uses total X-ray reflection in order to fulfill this need, is known.

When X-rays are incident at a critical angle or less on a sample having a flat surface, total reflection occurs at the surface of the sample. This angle is a low angle, and when CuKα-ray is used, the angle is about 0.22° for Si and about 0.57° for Au.

In FIG. 13A, X-rays are reflected at an angle α equal to the angle of incidence α when X-rays R1 are incident at a low angle α near the critical angle on the surface Sa of a sample S. Meanwhile, diffraction occurs on a lattice plane K perpendicular to the sample surface Sa, and the diffracted X-rays exit grazing the sample surface Sa. This diffraction phenomenon is generally referred to as in-plane diffraction. An apparatus for performing measurement in which this in-plane diffraction is detected by an X-ray detector is an in-plane X-ray diffractometer.

This in-plane X-ray diffractometer is disclosed in, e.g., Japanese Patent Application Laid-open No. 11-287773. In accordance with this in-plane X-ray diffractometer, diffraction from a lattice plane perpendicular to the surface of a thin film can be directly measured, consequently, the structure near the surface can be directly evaluated, and as a result, a sample can be accurately evaluated.

In accordance with this in-plane X-ray diffractometer, the depth to which the incident X-rays R1 penetrate the interior of the sample S is very minimal, as in several nm or less. Consequently, information from the substrate or undercoat can be substantially eliminated in the measurement results of a thin film, and as a result, a clear in-plane X-ray diffraction diagram can be obtained.

In the conventional in-plane X-ray diffractometer disclosed in Japanese Patent Application Laid-open No. 11-287773, a parallel slit analyzer (PSA) is provided between the sample and the X-ray detector, and overlapping of diffracted X-rays is prevented by the PSA to realize angular resolution. A clear X-ray diffraction diagram with high resolution is thereby obtained. However, this PSA itself tends to reduce the amount of X-rays considerably. Consequently, there is a problem in that it is difficult to obtain high-intensity in-plane diffracted X-rays in the in-plane X-ray diffractometer disclosed in Japanese Patent Application Laid-open No. 11-287773.

(In-Plane Reciprocal-Space Mapping Apparatus)

For example, Japanese Patent Application Laid-open No. 11-304729 discloses an in-plane reciprocal-space mapping apparatus. A plan view of the conventional in-plane reciprocal-space mapping apparatus is shown in FIG. 14. In FIG. 14, X-rays R0 emitted from an X-ray source F are incident at a small angle of incidence on the surface Sa of a sample S after having been converted into monochromatic and parallel X-rays R1 by an incidence-side optical system 101.

The incident X-rays R1 diffract at the lattice plane perpendicular to the sample surface Sa and become diffracted X-rays R2, proceeding in the almost grazing direction (i.e., in-plane direction) with respect to the sample surface Sa. Among the diffracted X-rays R2, only those at a predetermined diffraction angle are selected by a parallel slit analyzer (PSA) 103 (i.e., after having avoided the overlapping of diffracted X-rays, in other words, after having been endowed with angular resolution), and are thereafter received by an X-ray detector 104. The X-ray detector 104 outputs an electric signal that corresponds to the intensity of the received X-rays.

The X-ray detector 104 is a zero-dimensional X-ray detector. When reciprocal-space mapping measurement is to be carried out, the X-ray detector 104 is caused to carry out a [$2\theta_\chi$ (theta chi)/$\phi$]-scan at individual step angle positions while the sample S is rotated for $\phi$-rotation (i.e., in-plane rotation) in a stepwise fashion about the $\phi$-axis line (i.e., the line extending in the direction that passes through the sample s and passes through the plane of the drawing of FIG. 14).

A [$2\theta_\chi/\phi$]-scan is an operation such as the following. That is, first, the intensity of the diffracted X-rays is measured with the X-ray detector 104 in an initial angular position. Next, the X-ray detector 104 is slightly rotated (i.e., $2\theta_\chi$-scan rotation) about the $2\theta_\chi$-axis line, which is the same axis line as the $\phi$-axis line, and in accompaniment therewith, the intensity of the diffracted X-rays is measured by the X-ray detector 104 with the sample S rotated half of $2\theta_\chi$ about the $\phi$-axis line (i.e., $\phi$-rotation). Thereafter, $2\theta_\chi$-rotation, and $\phi$-rotation in coordination therewith, are executed continuously or a plurality of times in a stepwise fashion, and the intensity of the diffracted X-rays is measured by the X-ray detector 104 in each rotation angle position.

In accordance with the foregoing, the intensity information of the diffracted X-rays is acquired in a plurality of positions specified by the plurality of step-angle positions pertaining to the in-plane rotation φ and the plurality of angular positions pertaining to the 2θ$_χ$/φ-scan. This intensity information is plotted on two-dimensional coordinates to thereby obtain an in-plane reciprocal-space mapping diagram. Viewing this in-plane reciprocal-space mapping diagram allows the structure of a crystal plane in a thin film to be accurately ascertained.

Nevertheless, in the conventional in-plane reciprocal-space mapping apparatus disclosed in Japanese Patent Application Laid-open No. 11-304729, a parallel slit analyzer (PSA) 103 is provided in FIG. 14 for preventing the overlapping of in-plane diffracted X-rays R2 to realize angular resolution. The PSA tends to reduce the amount of X-rays considerably. Consequently, there is a problem in that it is difficult to obtain high-intensity in-plane diffracted X-rays in the in-plane reciprocal-space mapping apparatus disclosed in Japanese Patent Application Laid-open No. 11-304729.

(Grazing-Incidence Wide-Angle X-Ray Scattering/Small-Angle X-Ray Scattering Apparatus (GI-WAXS/SAXS Apparatus))

A GI-WAXS/SAXS apparatus is capable of both GI-WAXS measurement and GI-SAXS measurement. A GI-WAXS/SAXS apparatus causes small-diameter incident X-rays R1, which have been extremely narrowed, to be incident on a sample S at a low angle ω of almost grazing of the surface Sa of the sample S, and the scattered X-rays R3 emitted almost grazing the surface Sa are detected by an X-ray detector 105.

The apparatus for measuring the scattered X-rays R3 in a low-angle region is the GI-SAXS apparatus. The apparatus for measuring the scattered X-rays R3 in a high-angle region is the GI-WAXS apparatus. Following is the reason for narrowing the incident X-rays R1. That is, when the X-ray radiation field is widened on a sample, the scattered X-rays R3 spread out. When the scattered X-rays R3 spread out, there is overlapping of scattered X-rays R3 having different scattering angles, and as a result, the angular resolution is reduced. The reason that the X-rays R1 are narrowed is to prevent the scattered X-rays R3 from spreading out and having the scattered X-rays R3 overlapping each other, and to increase the angular resolution. The X-ray detector 105 is a two-dimensional X-ray detector. The X-ray detector 105 measures intensity of the scattered X-ray pertaining to in-plane direction of the sample (in-plane direction Qxy) and the normal direction of the sample (out-of-plane direction Qz).

In the GI-WAXS/SAXS apparatus shown in FIG. 15, the incident X-rays R1 must be shaped into a small-diameter X-ray beam in order to obtain a scattering image having high angular resolution. Consequently, it is difficult to obtain high-intensity scattered x-rays. As a result, there is a problem in that it is difficult to obtain a clear scattered x-ray diagram in a short period of time.

(X-Ray Diffractometer with X-Ray Shield Plate Disposed on a Sample)

Japanese Patent Application Laid-open No. 2002-310948 discloses an X-ray diffractometer with an X-ray shield plate disposed on a sample. In this conventional X-ray diffractometer, using reference symbols used in this Official Journal, incident X-rays exiting a second slit (2) pass through an aperture (11) in the X-ray shield plate (third slit 6) and are incident on the sample (S). Parasitic scattering X-rays generated from the second slit (2) are blocked in their progress by the shielding part of the X-ray shield plate (third slit 6) and do not arrive at the X-ray detector (7). The X-ray detector (7) is thereby exposed to scattered X-rays from the sample S, which is the object of measurement, without being disturbed by parasitic scattering X-rays.

The main effects of the X-ray shield plate (third slit 6) are to permit incident X-rays to be incident on the sample (S) by way of the aperture (11) and to prevent parasitic scattering X-rays generated by other slits from arriving at the X-ray detector (7) with the aid of the X-ray shield wall portion. Japanese Patent Application Laid-open No. 2002-310948 does not describe a technique for allowing specific X-rays from among the X-rays diffracted at the sample (S) to pass through the aperture (11) of the X-ray shield plate (third slit 6), and shielding diffracted X-rays other than the specific X-rays with the aid of the X-ray shield wall portion of the X-ray shield (third slit 6).

PATENT LITERATURE

[Patent Citation 1] Japanese Patent Application Laid-open No. 11-287773
[Patent Citation 2] Japanese Patent Application Laid-open No. 11-304729
[Patent Citation 3] Japanese Patent Application Laid-open No. 2002-310948

SUMMARY OF THE INVENTION

The present invention was devised in view of the problems described above in conventional apparatuses, and an object thereof is to provide a parallel-beam X-ray diffractometer, wherein (1) X-rays diffracted at the sample are prevented from spreading out by preventing the X-rays from overlapping each other, whereby a diffracted X-ray image with high resolution can be obtained by the X-ray detector, (2) high-intensity diffracted X-rays can be obtained even when X-ray overlapping is prevented as described above, and (3) obtaining a clear diffracted X-ray image with high resolution as described above is realized using a simple configuration.

(Solution 1) The X-ray diffractometer according to the present invention obtains X-ray diffraction angles of diffracted X-rays by detecting with an X-ray detector diffracted X-rays diffracted at a sample when X-rays are emitted at the sample at each angle of the angles about a center point of goniometer circles, the X-ray diffractometer being characterized in having an X-ray shield member provided with an X-ray passage port, the X-ray passage port allowing X-rays diffracted at the sample to pass so that the diffracted X-rays pass through the center point of the goniometer circles, and the X-rays diffracted at the sample being shielded by the X-ray shield member so that the diffracted X-rays pass through areas other than the center point of the goniometer circles.

The X-ray diffractometer is a parallel-beam X-ray diffractometer. The parallel-beam X-ray diffractometer is, e.g., an in-plane X-ray diffractometer, an in-plane reciprocal-space mapping apparatus, or a GI-WAXS/SAXS apparatus. In an in-plane X-ray diffractometer, an in-plane reciprocal-space mapping apparatus, and a GI-WAXS/SAXS apparatus, X-rays are incident at an incidence angle (i.e., a low incidence angle) that almost grazes or is very close to the surface of a sample.

In the above-described configuration, the "X-ray detector" may be a zero-dimensional X-ray detector that has no position resolution, a one-dimensional X-ray detector having rectilinear position resolution, and a two-dimensional X-ray detector having in-plane position resolution.

In the above-described configuration, the wording "the X-ray passage port allowing X-rays diffracted at the sample to pass so that the diffracted X-rays pass through the center point of the goniometer circles" includes the case in which diffracted X-rays pass through the center point itself and the case in which the X-rays pass near the center point. The term "near" in this case is set, as appropriate, in accordance with the degree of definition being sought in the diffraction image. In other words, when high definition is desired, the X-ray passage port is set so as to allow passage of only diffracted X-rays that pass through the center point itself or extremely close thereto of the goniometer circles. Conversely, when low definition is permitted, the X-ray passage port can be set so as to allow passage of diffracted X-rays that pass through an area slightly distant from the center point of the goniometer circles.

(Goniometer Circle)

In the above-described configuration, the term "goniometer circle" is a circular trajectory for moving an X-ray detector in order to detect X-rays diffracted at a sample. In other words, the X-ray detector in X-ray diffraction measurement rotatably moves along the goniometer circle about the center point of the goniometer circle. The X-ray detector in this case may be the zero-dimensional X-ray detector, the one-dimensional X-ray detector, or the two-dimensional X-ray detector.

A one-dimensional X-ray detector having rectilinear position resolution is formed by arranging a plurality of pixels, which are units for detecting X-rays, along a straight line. A two-dimensional X-ray detector having in-plane position resolution is formed by arranging a plurality of pixels, which are units for detecting X-rays, in a planar fashion. A one-dimensional X-ray detector and a two-dimensional X-ray detector identify angle information of diffracted X-rays using a plurality of pixels. Therefore, the diffraction angle of diffracted X-rays can be determined even when the X-ray detector is fixed in place and does not itself rotatably move in an area where a plurality of pixels exists.

In this case, it may possibly be interpreted that a goniometer circle as a circular trajectory for moving the X-ray detector does not exist.

However, when a one-dimensional X-ray detector or a two-dimensional X-ray detector is used and there is a desire to detect diffracted X-rays in areas outside of the area in which a plurality of pixels is present, the one-dimensional X-ray detector or two-dimensional X-ray detector itself must be moved to the desired area. In this case, the one-dimensional X-ray detector or two-dimensional X-ray detector must be moved along a circular trajectory. The circular trajectory in this case is a goniometer circle and the center point of the circular trajectory is the center of the goniometer circle.

In specific types of X-ray diffractometers, the one-dimensional X-ray detector or two-dimensional X-ray detector may be rectilinearly moved rather than rotatably moved in order to move the one-dimensional X-ray detector or two-dimensional X-ray detector itself to a desired area. In this case, it may possibly be interpreted that a goniometer circle as a circular trajectory for moving the X-ray detector does not exist.

However, even when a one-dimensional X-ray detector or two-dimensional X-ray detector are to be rectilinearly moved rather than rotatably moved in this fashion, it is possible to consider rotatably moving the one-dimensional X-ray detector or two-dimensional X-ray detector in an imaginary fashion, and it is therefore possible to specify a goniometer circle and a center point of the goniometer circle.

(Effects of the X-Ray Diffractometer According to the Present Invention Having the Above-Described Configuration)

(i) In measurement that uses a one-dimensional X-ray detector, a two-dimensional X-ray detector, or the like, X-rays diffracted at a sample and that advance toward the detector must be reduced in width in order to make use of the position resolution of the detector. In general, the width of diffracted X-rays is affected by the size of the irradiated area on the sample and X-rays spread out, and it is therefore difficult to obtain high-resolution data under such conditions. Also, it is not possible to obtain a correct diffraction angle when diffracted X-rays which have not passed near the center of the goniometer circle are detected by a detector (e.g., one-dimensional X-ray detector or two-dimensional X-ray detector) having position resolution. In the present invention, the position resolution at the detector position is enhanced by both selecting only diffracted X-rays that pass near the center of the goniometer circle in order to obtain a correct diffraction angle and reducing the width of the diffracted X-rays.

(ii) Only X-rays that pass through or near the center point of the goniometer circle are sent into the X-ray detector. Therefore, X-rays diffracted at the sample can be prevented from spreading out, and as a result, X-rays diffracted at the sample can be prevented from overlapping each other. As a result, an X-ray diffraction diagram having high resolution can be obtained by the X-ray detector.

(iii) Among the X-rays diffracted within a wide area of the sample, diffracted X-rays that have congregated near the center point of the goniometer circle are sent into the X-ray detector, and high-intensity diffracted X-rays can be obtained even when spreading out and overlapping of X-rays has been prevented as in (ii) above. A clear X-ray diffraction diagram can be obtained thereby.

(iv) Since an X-ray shield member provided with an X-ray passage port is merely disposed near the surface of the sample, the configuration is very simple.

(v) In the X-ray diffractometer of Japanese Patent Application Laid-open No. 2002-310948, it is disclosed that, using reference symbols used in this Official Journal, a third slit (6) as an X-ray shield member is disposed on the surface of the sample (S). However, the third slit (6) causes X-rays which have passed through the second slit (2) to pass through by the aperture (11) and proceed towards the sample (S), and shields parasitic scattering rays generated at the second slit (2). The third slit (6) is a completely different member from the X-ray shield member of the present invention.

Japanese Patent Application Laid-open No. 2002-310948 does not disclose that the aperture (11) is provided near the center point of a goniometer circle. Also, Japanese Patent Application Laid-open No. 2002-310948 does not describe the technical concept of allowing specific X-rays among the X-rays diffracted at the sample to pass using an aperture (11) and shields X-rays other than the specific X-rays using a third slit (6).

(Solution 2) In another aspect of the present invention, the X-ray passage port is disposed on the center point of the goniometer circle. The phrase "on the center point" refers to cases such as the case in which the X-ray passage port is in a position that covers the center point (i.e., a position in which the X-ray passage port includes the center point), and the case in which the X-ray passage port is slightly offset from the center point yet in a position near the center point such that desired angular resolution can be obtained by the X-ray detector.

Providing an X-ray passage port on the center point of a goniometer circle makes it possible for X-rays diffracted at the sample and X-rays attempting to pass near the center point of the goniometer circle to reliably pass through the X-ray passage port. Diffracted X-rays other than X-rays that pass near the center point of the goniometer circle can be reliably shielded by the X-ray shield member.

(Solution 3) In yet another aspect of the present invention, the X-ray shield member is disposed in contact with the surface of the sample or near the surface of the sample. As used herein, the meaning of the term "near" includes the X-ray shield member being set at a slight distance from the surface of the sample in a range that allows a desired angular resolution to be obtained by the X-ray detector even though the X-ray shield member is set at a slight distance from the surface of the sample.

(Solution 4) In yet another aspect of the present invention, the X-ray shield member is disposed in contact with the end face of the sample on the X-ray detector side, or near the end face of the sample on the X-ray detector side. As used herein, the meaning of the term "near" includes the X-ray shield member being set at a slight distance from the end face of the sample in a range that allows a desired angular resolution to be obtained by the X-ray detector even though the X-ray shield member is set at a slight distance from the end face of the sample.

(Solution 5) In yet another aspect of the present invention, the X-ray passage port is a pinhole extending in the direction intersecting the sample, or a slit extending in the direction intersecting the sample. The pinhole is a hole having a circular, semicircular, square, rectangular, triangular, or other polygonal shape. The slit is a long, groove-shaped hole.

(Solution 6) In yet another aspect of the present invention, the X-rays incident on the sample are line-focus X-rays having a cross-sectional shape in which the longitudinal direction is short and the lateral direction is long, and the lengthwise direction (i.e., the lateral direction) of the line focus is the direction parallel to the surface of the sample.

When a sample has been irradiated by point-focus X-rays having a cross-sectional shape that is short in both the longitudinal direction and the lateral direction, the surface area of the sample irradiated by the X-rays is low and it is not possible to bring out many X-rays from the sample. In contrast, irradiating a sample with line-focus X-rays makes it possible to increase the surface area of the sample irradiated by X-rays. Consequently, high-intensity diffracted X-rays can be obtained.

(Solution 7) In yet another aspect of the present invention, X-rays are caused to be incident at a low angle with respect to the sample so that diffraction occurs on a lattice plane perpendicular to the surface of the sample. This configuration allows measurement of in-plane X-ray diffraction to be carried out.

(Solution 8) Yet another aspect of the present invention has an $\omega$-rotation system for adjusting the incidence angle of X-rays on the sample, a $\phi$-rotation system for rotating the sample in-plane, a $2\theta$-rotation system for moving the X-ray detector in the out-of-plane direction, and a $2\theta_\chi$-rotation system for moving the X-ray detector in the in-plane direction, the $\omega$-rotation system, the $\phi$-rotation system, the $2\theta$-rotation system, and the $2\theta_\chi$-rotation system operating about the center point, as an origin, of the goniometer circle, which is a shared center point. In accordance with this aspect, it is possible to carry out measurement by in-plane reciprocal-space mapping.

EFFECTS OF THE INVENTION (i) In measurement that uses a one-dimensional X-ray detector, a two-dimensional X-ray detector, or the like, X-rays diffracted at a sample and that advance toward the detector must be reduced in width in order to make use of the position resolution of the detector. In general, the width of diffracted X-rays is affected by the size of the irradiated area on the sample and X-rays spread out, and it is therefore difficult to obtain high-resolution data under such conditions. Also, it is not possible to obtain a correct diffraction angle when diffracted X-rays which have not passed near the center of the goniometer circle are detected by a detector (e.g., one-dimensional X-ray detector or two-dimensional X-ray detector) having position resolution. In the present invention, the position resolution at the detector position is enhanced by both selecting only diffracted X-rays that pass near the center of the goniometer circle in order to obtain a correct diffraction angle and reducing the width of the diffracted X-rays.

(ii) Only X-rays that pass through or near the center point of the goniometer circle are sent into the X-ray detector. Therefore, X-rays diffracted at the sample can be prevented from spreading out, and as a result, X-rays diffracted at the sample can be prevented from overlapping each other. As a result, an X-ray diffraction diagram having high resolution can be obtained by the X-ray detector.

(iii) Among the X-rays diffracted within a wide area of the sample, diffracted X-rays that have congregated near the center point of the goniometer circle are sent into the X-ray detector, and high-intensity diffracted X-rays can be obtained even when spreading out and overlapping of X-rays has been prevented as in (ii) above. A clear X-ray diffraction diagram can be obtained thereby.

(iv) Since an X-ray shield member provided with an X-ray passage port is merely disposed near the surface of the sample, the configuration is very simple.

BRIEF DESCRIPTION OF THE DRAWINGS

FIG. 11 is a two-dimensional image showing measurement results obtained using the X-ray diffractometer according to the present invention in FIG. 8;

DESCRIPTION OF THE PREFERRED EMBODIMENTS

Figure 1:
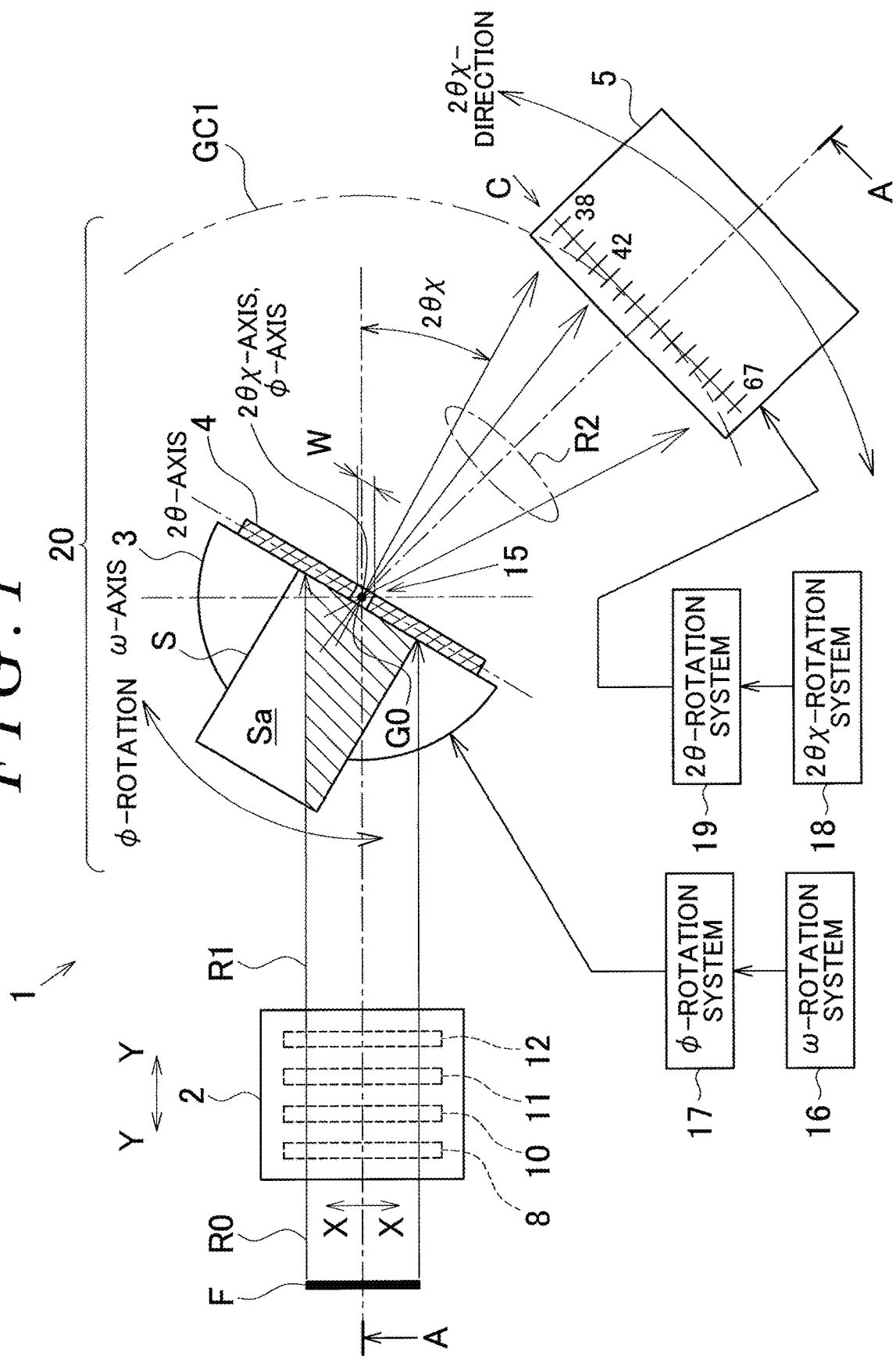
FIG. 1 is a plan view of an embodiment of the X-ray diffractometer according to the present invention.

The X-ray diffractometer according to the present invention will be described hereinbelow on the basis of embodiments. As shall be apparent, the present invention is not limited to these embodiments. Also, in the drawings attached to the present specification, the constituent elements may be shown in a scale that differs from the actual components in order to facilitate understanding of the characteristic portions.

First Embodiment of the X-Ray Diffractometer

Figure 2:
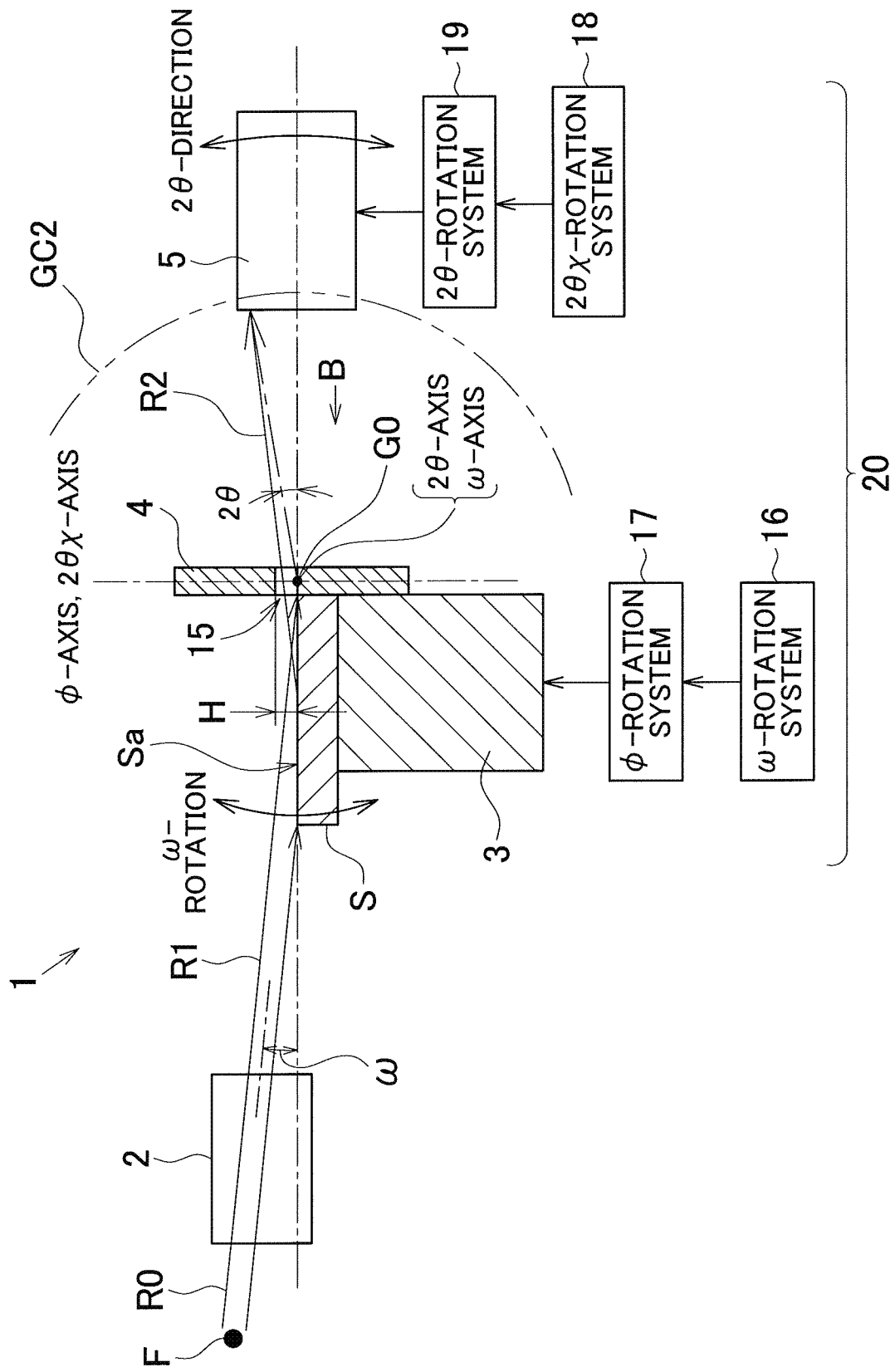
FIG. 2 is a lateral cross-sectional view along the line A-A of the X-ray diffractometer of FIG. 1.

FIGS. 1 and 2 show an embodiment of an in-plane reciprocal-space mapping apparatus, which is an embodiment of the X-ray diffractometer according to the present invention. FIG. 1 is a plan view of an in-plane reciprocal-space mapping apparatus, and FIG. 2 is a side view along the line A-A of FIG. 1. In FIG. 2, the cross-sectional structure of non-essential portions is omitted.

The in-plane reciprocal-space mapping apparatus simultaneously performs measurement by in-plane diffraction and measurement by reciprocal-space mapping. Measurement by in-plane diffraction and measurement by reciprocal-space mapping are as follows.

(In-Plane Diffraction Measurement)

Figure 13A:
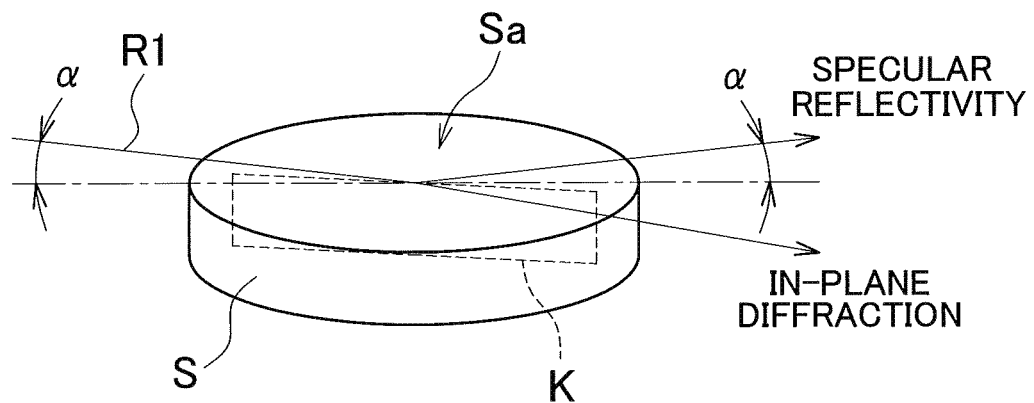
FIGS. 13A and 13B are drawings illustrating in-plane diffraction and out-of-plane diffraction.
Figure 13B:
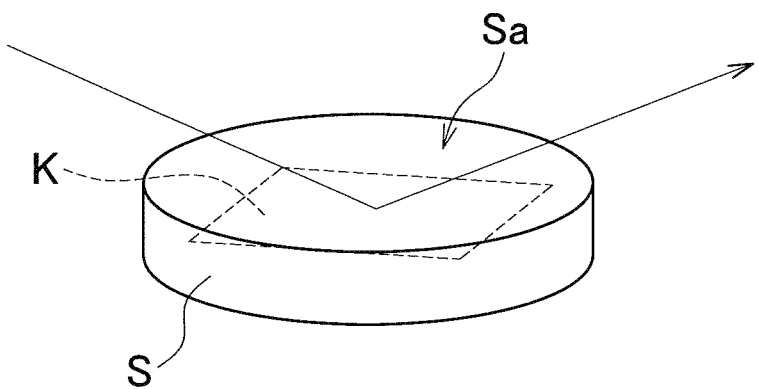
Figure 14:
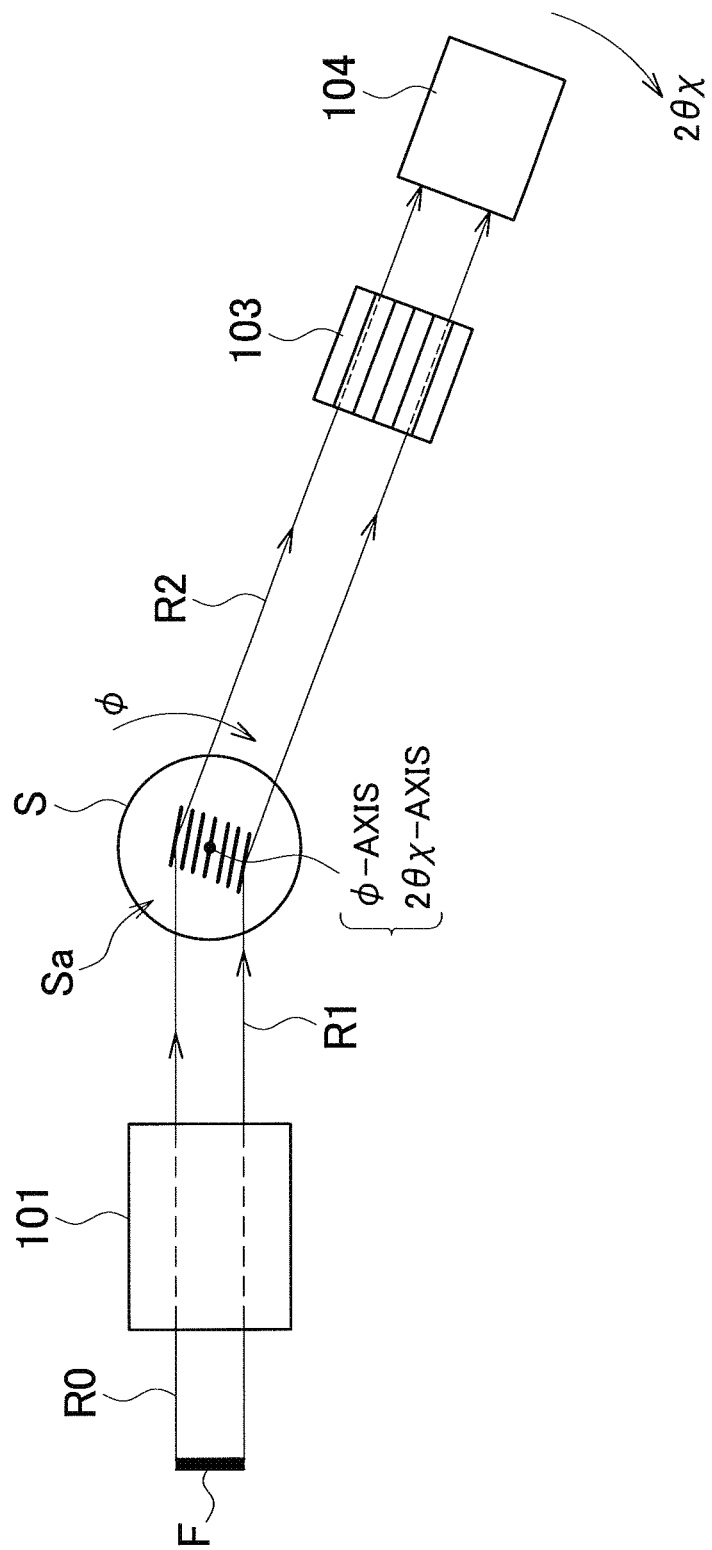
FIG. 14 is a plan view showing an example of a conventional in-plane reciprocal-space mapping apparatus.

An X-ray diffraction measurement method includes out-of-plane measurement and in-plane measurement depending on the direction of the lattice plane to be measured. Out-of-plane measurement is a technique for evaluating a lattice plane K which is not perpendicular to the surface Sa of the sample S as shown in FIG. 13B. In-plane measurement is a technique for evaluating a lattice plane K which is perpendicular to the surface Sa of the sample S as shown in FIG. 13A.

In out-of-plane measurement, incident X-rays and an X-ray detector are scanned in an angle range of, e.g., about 5° to 90°, and information about crystal structure is obtained from the diffracted X-rays. The incident X-rays are able to penetrate to a relatively deep area such as a depth of several tens of micrometers of the sample and may therefore be buried in the base signal when the signals of diffracted X-rays derived from a thin film are weak.

In contrast, in-plane measurement is carried out with the incident angle of X-rays fixed at a small angle (e.g., 0.2° to 0.5°) near the critical angle of full reflectance. Consequently, the depth of penetration of X-rays into the sample is several tens of nanometers, and the signal of the diffracted X-rays is detected with high precision and is unaffected by the substrate.

(Reciprocal-Space Mapping Measurement)

In general, the X-ray diffraction conditions can be considered in accordance with direction of lattice planes and interplanar spacing of lattice planes. The direction of lattice-planes can be expressed by the normal line of lattice planes. The interplanar spacing can be set as a vector that is equal to, e.g., $2\pi$ times the reciprocal of the interplanar spacing. Lattice points are formed by the set of distal end points of vectors in which the length and direction have been determined in this fashion. The space formed by these lattice points has a dimension that is the reciprocal of the length as noted above and is therefore referred to as a "reciprocal space." The thusly formed lattice is referred to as a "reciprocal lattice." The distal end points of a reciprocal lattice are referred to as "reciprocal lattice points."

Reciprocal-space mapping measurement is a method for measuring the intensity distribution of reflected rays from a crystal in a reciprocal space. A reciprocal-space mapping diagram obtained by reciprocal lattice mapping measurement represents in two dimensions the interplanar spacing of lattice planes and the distribution of crystal orientation both in a crystalline substance.

(In-Plane Reciprocal-Space Mapping Measurement)

According to in-plane reciprocal-space mapping measurement, since X-rays are caused to make almost grazing incidence on the surface of a thin-film sample in in-plane diffraction measurement, i.e., since X-rays are incident on surface of a thin-film sample at a very low angle, signals from a film with low thickness can be efficiently captured. At the same time, by collecting signals while the orientation of the sample is changed in small steps in reciprocal-space mapping measurement, information about crystal orientation can be obtained. In other words, according to in-plane reciprocal-space mapping measurement, it is possible to accurately capture information about crystal orientation in relation to a thin-film sample.

(Configuration of an In-Plane Reciprocal-Space Mapping Apparatus)

In FIGS. 1 and 2, an in-plane reciprocal-space mapping apparatus 1 of the present embodiment has an X-ray source F, and an incidence-side optical system 2, a sample stage 3, a pinhole member 4 as an X-ray shield member, and a two-dimensional X-ray detector 5.

The X-ray source F generates x-rays having a long and thin X-ray focal point, i.e., line-focus. The lengthwise direction of the X-ray source F is the direction parallel to the surface Sa of the sample S, as shown in FIGS. 1 and 2.

The incidence-side optical system 2 has, e.g., in sequence from the X-ray source F side, a paraboloidal multilayer mirror 8, an in-plane parallel slit collimator (PSC) 10, a longitudinal limitation slit 11, and an incidence slit 12. The incidence-side optical system 2 may be formed in combination with other X-ray optical elements as required.

The paraboloidal multilayer mirror 8 is formed by layering a plurality of heavy-element layers and a plurality of light-element layers in alternating fashion, and is an X-ray mirror in which the surface for reflecting X-rays is a paraboloid. The X-rays R0 emitted from the X-ray source F are made into monochromatic X-rays by the paraboloidal multilayer mirror 8 and are simultaneously made into parallel X-rays.

The in-plane PSC 10 is a PSC for restricting the spreading of X-rays in the in-plane direction. The in-plane PSC 10 is basically the same structure as so-called a soller slit. Specifically, the in-plane PSC 10 is an X-ray optical element obtained by a lining up several thin X-ray shield members extending in the direction that passes through the plane of the drawing of FIG. 1 and the direction of progress (Y-Y direction) of X-rays, so to be parallel to each other in the X-X direction (the direction crosswise to the X-ray optical path). The parallelism of the X-rays in the lengthwise direction is increased by the in-plane PSC 10.

The longitudinal limitation slit 11 limits spreading in the longitudinal direction (direction parallel to the plane of the drawing of FIG. 1, i.e., the in-plane direction) for X-rays which have exited the in-plane PSC 10. The incidence slit 12 limits the beam size in the lateral direction (the direction perpendicular to the plane of the drawing of FIG. 1) for X-rays which have exited the longitudinal limitation slit 11.

The top surface of the sample stage 3 is a sample placement surface. The sample S is disposed on the sample placement surface. The sample S is bonded to the sample stage 3 as required. The sample S is a substance obtained by forming a thin film on a substrate. The substrate of the sample S is placed on the sample stage 3. X-rays are irradiated onto the top surface of the sample S. The present in-plane reciprocal-space mapping apparatus 1 captures information about the crystal orientation and the interplanar spacing of lattice planes in relation to the thin film of sample S.

The pinhole member 4 as the X-ray shield member is formed by a single plate member formed by a material difficult for X-rays to penetrate. A pinhole 15 as an X-ray passage port is formed in the interior of the pinhole member 4, in the present embodiment, substantially the center. In the present embodiment, the pinhole member 4 is supported by the sample stage 3.

The pinhole member 4 may be supported by the X-ray detector 5 rather than the sample stage 3. The pinhole member 4 may furthermore be supported by any structure other than the sample stage 3 and the X-ray detector 5. However, the sample stage 3 must be capable of horizontal and rotational movement, and the pinhole 15 in the pinhole member 4 must constantly maintain the center position of a later-described goniometer circle.

In FIG. 1, the X-rays R1 which have exited the incidence-side optical system 2 irradiate the area of the surface Sa of the sample S indicated by the shaded portion. At this time, among the X-rays diffracted at the crystal lattice plane (see reference symbol K of FIG. 13A) present in the sample S in a direction perpendicular to the surface Sa, only X-rays that have passed through the pinhole 15 proceed toward the X-ray detector 5. It is thereby possible to limit the spreading out of diffracted X-rays R2 in accordance with the size of the X-ray irradiation field on the sample S, and the overlapping of diffracted X-rays R2 having different diffraction angles. As a result, diffracted X-rays are detected with high angular resolution by the X-ray detector 5.

In other words, the pinhole 15 feeds to the X-ray detector 5 only X-rays that have passed near the center of the goniometer circle among the X-rays diffracted at a specific angle from the sample S. Meanwhile, X-rays that do not pass near the center of the goniometer circle are shielded by the X-ray shield portion of the pinhole member 4 as the X-ray shield member. It is thereby possible to prevent the spreading out and overlapping of diffracted X-rays, and allows measurement with high angular resolution.

The diffracted X-rays R2, in which the spreading out and overlapping of diffracted X-rays is limited, are received in the two-dimensional X-ray detector 5. The two-dimensional X-ray detector 5 outputs an electric signal that corresponds to the intensity of the received X-rays. The two-dimensional X-ray detector 5 is formed using a charge coupled device (CCD) X-ray detector, a photon-counting-type X-ray detector, or the like.

The CCD X-ray detector is made up of a plurality of CCD photoelements lined up in a planar fashion, i.e., two-dimensionally. The CCD photoelements may be elements that detect light in which X-rays have been converted to light and then converted to an electric signal, or may be elements that receive X-rays and directly convert the X-rays to an electric signal. A photon-counting-type X-ray detector is obtained by lining up a plurality of photo-counting elements in a planar fashion. The photon-counting elements receive X-rays and directly convert the X-rays to an electric signal. A single unit of the CCD photoelements and photon-counting elements is referred to as a pixel. The X-ray detector 5 can also be a one-dimensional X-ray detector in place of the two-dimensional X-ray detector. In FIG. 1, the symbol C drawn at the distal end section of the X-ray detector 5 schematically shows the angular scale.

In the present embodiment in FIG. 2, the bottom side of the pinhole 15 is disposed in the same height position as the surface Sa of the sample S. The pinhole 15 is a dot shape, which is not slit shaped as viewed from the direction of the arrow B, and is formed in, e.g., a square shape, rectangular shape, circular shape, semicircular shape, or any other dot shape. The pinhole 15 may also be a slit, which is a groove-shaped hole.

The width W of the 15 in FIG. 1 is determined in accordance with purpose, and may be, e.g., about the same as the width of a pixel of the two-dimensional X-ray detector 5 up to a width about 100 times the width of the pixel. When the pixel width of the X-ray detector 5 is 25 µm, the width W of the pinhole 15 is 25 µm to 2.5 mm. However, a pinhole having a width W that is about 10 times the pixel width is generally used in view of the relationship between the angular resolution and X-ray intensity.

(Drive System)

In FIGS. 1 and 2, an ω-rotation system 16 and a φ-rotation system 17 are connected to the sample stage 3. Meanwhile, a $2\theta_\chi$(theta chi)-rotation system 18 and a 2θ-rotation system 19 are connected to the X-ray detector 5. The ω-rotation system 16, φ-rotation system 17, $2\theta_\chi$-rotation system 18, and 2θ-rotation system 19 constitute a goniometer 20 (i.e., an angle-measuring device).

The φ-rotation system 17 rotates the sample stage 3 about the center of the φ-axis. This rotation of the sample stage 3 is referred to as φ-rotation. The φ-axis is an imaginary line extending in the direction that passes through the plane of the drawing of FIG. 1 (i.e., the vertical direction of FIG. 2). φ-Rotation is used for in-plane rotation of the sample S placed on the sample stage 3.

The ω-rotation system 16 rotates the sample stage 3 about the ω-axis in FIG. 1. This rotation of the sample stage 3 is referred to as ω-rotation. The ω-axis is the axis parallel to the plane of the drawing in FIG. 1 and is perpendicular to the direction of progress of the X-rays R1 incident on the sample S. ω-Rotation is used for changing the incidence angle ω of the X-rays R1 in relation to the sample S: the X-rays R1 being incident on the sample S placed on the sample stage 3.

The φ-rotation system 17 is placed on the ω-rotation system 16. In other words, when the ω-rotation system 16 operates, the sample stage 3 undergoes ω-rotation about the ω-axis, and simultaneously, the φ-rotation system 17 also rotates in integral fashion with the sample stage 3. On the other hand, when the φ-rotation system 17 operates, the sample stage 3 undergoes φ-rotation about the φ-axis, but the ω-rotation system 16 does not move.

The 2θ-rotation system 19 rotates the X-ray detector 5 about the 2θ-axis. This rotation of the X-ray detector 5 is referred to as 2θ-rotation. 2θ-Rotation is rotation in the out-of-plane direction. The 2θ-axis is the axis parallel to the plane of the drawing in FIG. 1 (in FIG. 2, the axis extending in the direction crosswise to the plane of the drawing). 2θ-Rotation is used for rotatably moving the X-ray detector 5 in the direction of the Qz-axis in the reciprocal space. This 2θ-rotation is used for adjusting the position of the X-ray detector 5.

The $2\theta_\chi$-rotation system 18 rotates the X-ray detector 5 about the $2\theta_\chi$-axis. This rotation of the X-ray detector 5 is referred to as $2\theta_\chi$-rotation. $2\theta_\chi$-Rotation is rotation in the in-plane direction. The $2\theta_\chi$-axis is the axis extending in the direction that passes through the plane of the drawing of FIG. 1 (the vertical direction of the plane of the drawing of FIG. 2). $2\theta_\chi$-Rotation is used for rotatably moving the X-ray detector 5 in the direction of the Qxy-axis in the reciprocal space. This $2\theta_\chi$-rotation is used for adjusting the position of the X-ray detector 5.

The ω-axis, φ-axis, 2θ-axis, and $2\theta_\chi$-axis all pass through the center point G0 of the goniometer circle GC1. In other words, these axes intersect at the center point G0 of the goniometer circle GC1. In the two-dimensional X-ray detector 5 used in the present embodiment, angular measurement is carried out by a pixel-reading operation. Therefore, the two-dimensional X-ray detector 5 is not required to be moved as long as X-ray detection is carried out in a range in which pixels are present. However, the two-dimensional X-ray detector 5 must be moved to a desired area when the area where X-rays are to be detected is outside of the area where pixels are present. Consequently, in the present embodiment, the two-dimensional X-ray detector 5 is configured so as to be capable of rotatably moving about the point G0. The trajectory of rotational movement of the two-dimensional X-ray detector 5 is the circle indicated by the symbol GC1, and the center point of the circle GC1 is the point G0. The circle GC1 is referred to as a goniometer circle and the point G0 is the center point of the goniometer circle. In this case, the diffraction angle measured by the two-dimensional X-ray detector 5 is the angle $2\theta_\chi$ along the goniometer circle GC1 about the center point G0.

The goniometer circle is not limited to the goniometer circle GC1 along the in-plane direction ($2\theta_\chi$-direction) shown in FIG. 1, and it is also possible to consider the direction perpendicular (i.e., the out-of-plane direction (2θ-direction)) to the in-plane direction ($2\theta_\chi$-direction), as shown by the symbol GC2 in FIG. 2. The center point of the goniometer circle GC2 of this out-of-plane direction (2θ-direction) is also the same point as the center point G0 of the goniometer circle GC1 along the in-plane direction ($2\theta_\chi$-direction).

In the present embodiment, the pinhole member 4 is disposed in contact or close contact with the end face or the distal end of the sample S on the X-ray detector 5 side, or is disposed near the end face thereof. The pinhole 15 is disposed on the center point G0 of the goniometer circle GC1 and the goniometer circle GC2. In other words, the pinhole 15 is disposed so as to cover the center point G0. Alternatively, the pinhole 15 is disposed so as to include the center point G0.

The rotation systems 16, 17, 19, and 18 relating to the ω-axis, φ-axis, 2θ-axis, and $2\theta_\chi$-axis are composed of a rotating machine (e.g., servomotor and pulse motor) in which the rotational angle can be controlled with high precision, a worm gear (a combination of a worm and worm wheel) for transmitting rotary power, or the like.

(Operation of the In-Plane Reciprocal-Space Mapping Apparatus)

In FIGS. 1 and 2, the sample S is placed on the sample stage 3. The sample S is a flat-shaped substance in which, e.g., an epitaxial thin film composed of (Pb, La)TiO3/Pt/MgO has been formed on the surface. The distal end of the sample S, i.e., the end face is in contact or close contact with the side surface of the pinhole member 4. Alternatively, the distal end of the sample S, i.e., the end face is disposed near the side surface of the pinhole member 4. Next, the ω-rotation system 16 is actuated to set the X-ray incidence angle ω to a low angle that is slightly less than the critical angle of full reflectance of the sample. Furthermore, the angle of the X-ray detector 5 in the in-plane direction is set to a predetermined angle that corresponds to the crystal lattice plane in the thin film of the sample S.

In this state, X-rays are emitted from the X-ray source F and the area of the sample S indicated by shading in FIG. 1 is irradiated by X-rays. X-rays diffracted at a lattice plane facing a predetermined direction in the thin film pass through the pinhole 15 and are taken into the X-ray detector 5, which is a two-dimensional X-ray detector. Angular resolution is imparted to the diffracted X-rays R2 by the pinhole 15, and the X-ray detector 5 therefore detects X-ray intensity at a known in-plane diffraction angle. At this time, the two-dimensional X-ray detector 5 simultaneously detects the X-ray intensity in a plurality of $2\theta_\chi$ positions by numerous pixels disposed in a plane.

Detection of X-ray intensity of the above numerous points in relation to a single φ-step angle is simultaneously carried out, and the φ-angle is thereafter rotated by a predetermined step to vary the orientation of the crystal lattice plane. The X-ray intensity in the $2\theta_\chi$-direction is detected for numerous cycles again in the varied direction. This work for detecting X-ray intensity is carried out at φ-steps in a predetermined angle range. The two-dimensional X-ray detector 5 is rotatably moved along the goniometer circle GC1 about the center point G0 as required. In-plane reciprocal-space mapping measurement is carried out in accordance with the foregoing.

Figure 3:
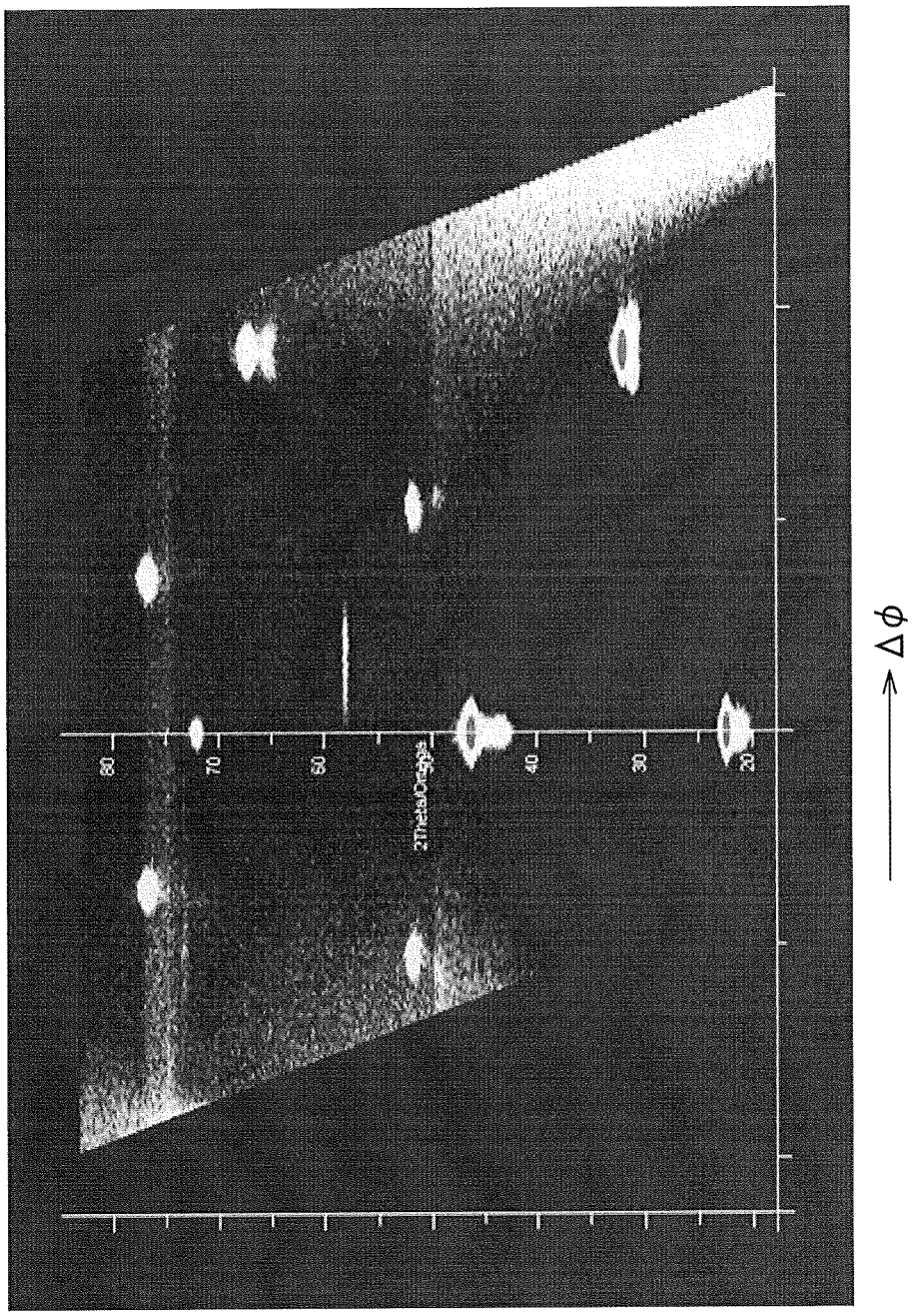
FIG. 3 is a view showing a diffraction diagram as the measurement results obtained by the X-ray diffractometer of FIGS. 1 and 2.
Figure 4:
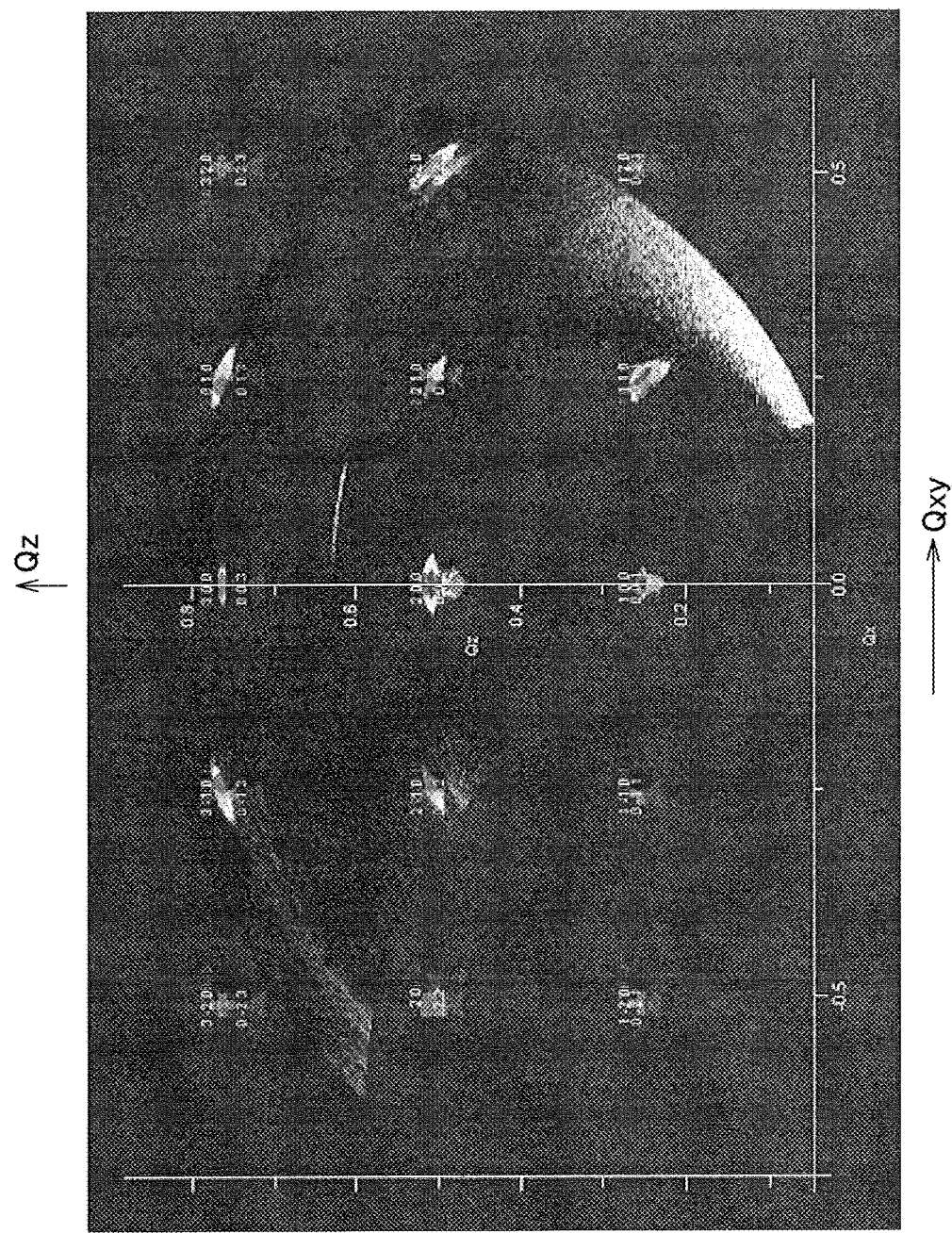
FIG. 4 is a view in which the diffraction diagram of FIG. 3 has been converted to a reciprocal-space mapping diagram.

When the X-ray intensity in the numerous measurement points determined in the foregoing manner is rendered as a two-dimensional map by a known drawing software program, a mapping diagram of "$2\theta_\chi$-to-φ" as shown in FIG. 3 is obtained (i.e., a $2\theta_\chi$ vs φ-mapping diagram or a $2\theta_\chi$ versus φ-mapping diagram). When the mapping diagram of "$2\theta_\chi$-to-φ" is converted to reciprocal space coordinates by a known conversion software program, and the reciprocal-space mapping diagram shown in FIG. 4 is obtained. In the diagram, numbers such as (3 −2 0), (3 −1 0), . . . indicate the plane index of a lattice plane.

In the reciprocal-space mapping diagram shown in FIG. 4, the crystal structure in the thin film of the sample S can be known by observing the positions of reciprocal lattice points. The X-ray diffraction diagram shown in FIG. 3 can be obtained by exchanging the X-ray detector 5 in FIG. 1 for a zero-dimensional counter (i.e., a counter without resolution) such as a scintillation counter (SC), and thereafter actually moving the zero-dimensional counter so as to perform a $2\theta_\chi$-scan.

In the present embodiment, mutual overlapping of diffracted X-rays R2 is limited by the pinhole member 4 as the X-ray shield member in contact or close contact with the sample S or by the pinhole member 4 as the X-ray shield member provided near the sample S, to thereby realize high angular resolution. Therefore, the angles can be accurately measured by the two-dimensional X-ray detector 5. When a zero-dimensional X-ray detector is used in place of a two-dimensional X-ray detector 5, it is possible to consider imparting angular resolution to the diffracted X-rays R2 by providing a PSA in an immediate anterior position, but in this case, the X-rays are likely to be reduced in intensity by the PSA. In contrast, in the present embodiment, the pinhole member 4 is provided in contact, close contact, or otherwise near the sample S, whereby diffracted X-rays can be acquired from a wide area (the area indicated by shading) of the surface Sa of the sample S in FIG. 1, and it is therefore possible to supply high-intensity diffracted X-rays to the X-ray detector 5.

When a zero-dimensional counter is used, measurement time requires about 13 hours. In contrast, in accordance with the in-plane reciprocal-space mapping apparatus of the present embodiment, numerous data can be obtained at one time by the two-dimensional X-ray detector 5, and measurement time is about one hour. This time can be further reduced to about 15 minutes by further optimizing the measurement conditions.

Thus, in accordance with the present embodiment, high-intensity diffracted X-rays can be obtained by a very simple configuration in that the pinhole member 4, which is a single plate member, is secured to the sample stage 3, and the pinhole 15 is disposed on the center point G0 of the goniometer circles GC1 and GC2.

(Modifications)

In the embodiment shown in FIGS. 1 and 2, the pinhole member 4 is mounted on the sample stage 3 so that the side surface of the pinhole member 4 as the X-ray shield member is in contact or close contact with the distal end, i.e., the end face of the sample S, or so that the side surface of the pinhole member 4 is positioned near the distal end, i.e., the end face of the sample S. In other words, the embodiment configured so that the sample S does not project toward the X-ray detector 5 side more than does the pinhole member 4.

Figure 5A:
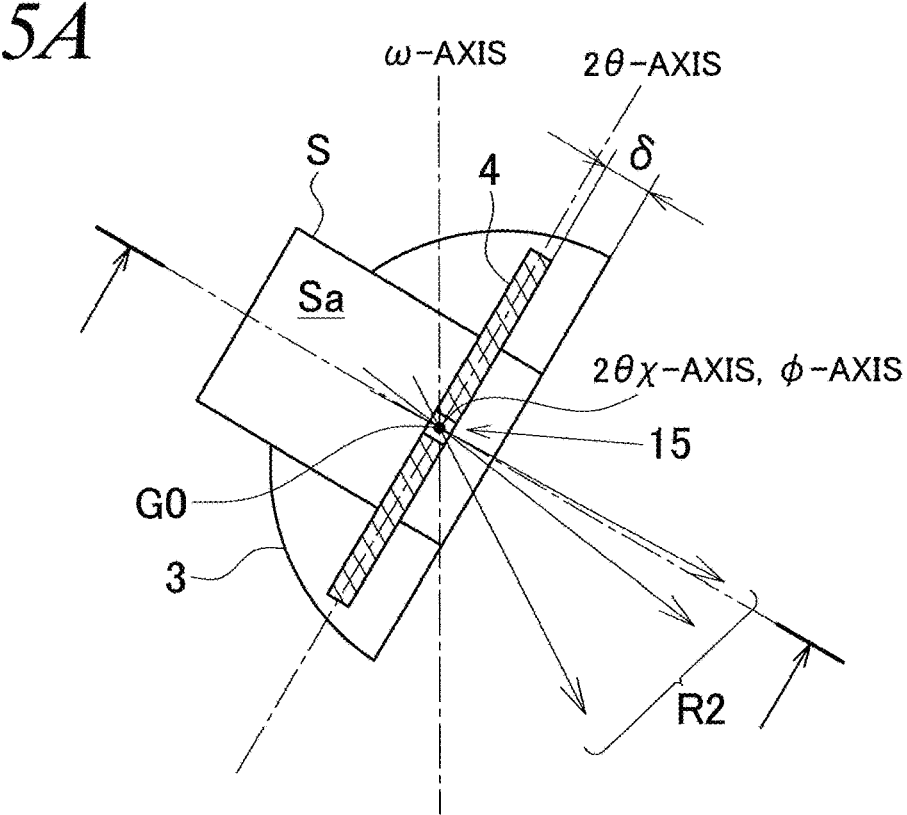
FIG. 5A is a plan view of another embodiment of the X-ray diffractometer according to the present invention.
Figure 5B:
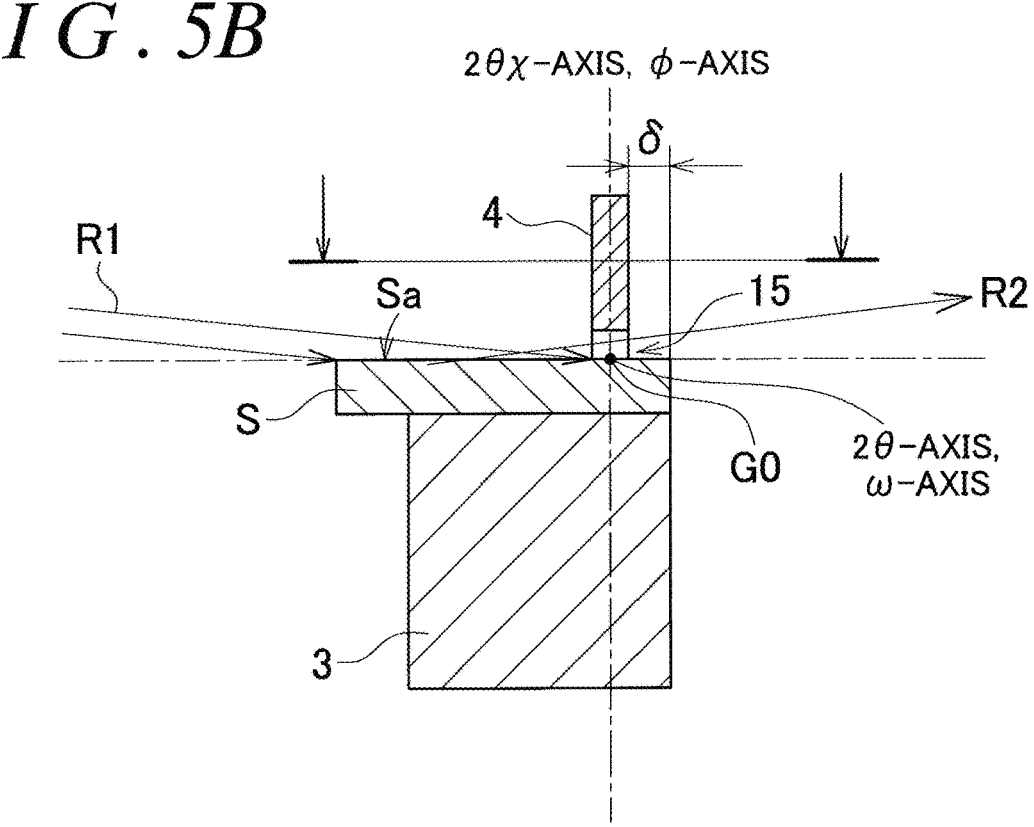
FIG. 5B is a lateral cross-sectional view of the embodiment of FIG. 5A.

However, in lieu thereof, the bottom surface of the pinhole member 4 may be in contact or close contact with the surface Sa of the sample S, and alternatively, the bottom surface of the pinhole member 4 may be positioned near the surface Sa of the sample S, as shown in FIGS. 5A and 5B. The pinhole member 4 may be supported by the sample stage 3 or may be supported by a component other than the sample stage 3. In the present modification, the distal end of the sample S projects to the X-ray detector 5 side (see FIGS. 1 and 2) side more greatly than does the pinhole member 4 by a dimension 8.

In the present modification as well, the spreading and overlapping of diffracted X-rays is limited by the pinhole member 4 and high angular resolution is obtained. Also, in the present modification as well, the intensity of diffracted X-rays can be increased by irradiation of X-rays in a wide area of the sample S, and the high intensity diffracted X-rays can be extracted with high efficiency by way of the pinhole 15.

In the present modification as well, the intersecting point of the ω-axis, 2θ-axis, $2\theta_\chi$-axis, and φ-axis is the center point G0 of the goniometer circles GC1, GC2 (see FIGS. 1 and 2). The pinhole member 4 is disposed in a position that includes the center point G0 of the goniometer circles GC1, GC2.

Second Embodiment of the X-Ray Diffractometer

Figure 6:
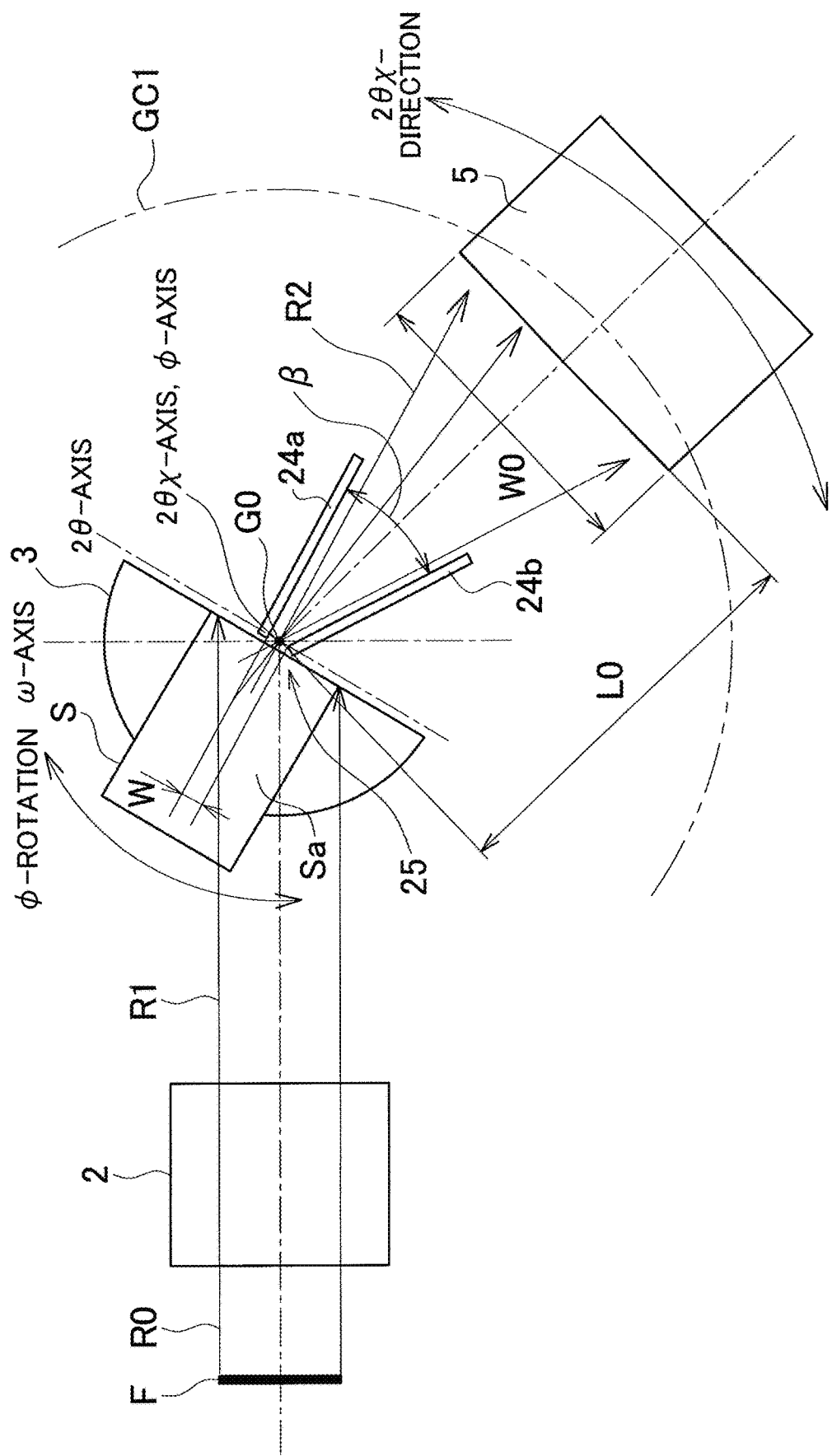
FIG. 6 is a plan view of yet another embodiment of the X-ray diffractometer according to the present invention.
Figure 7:
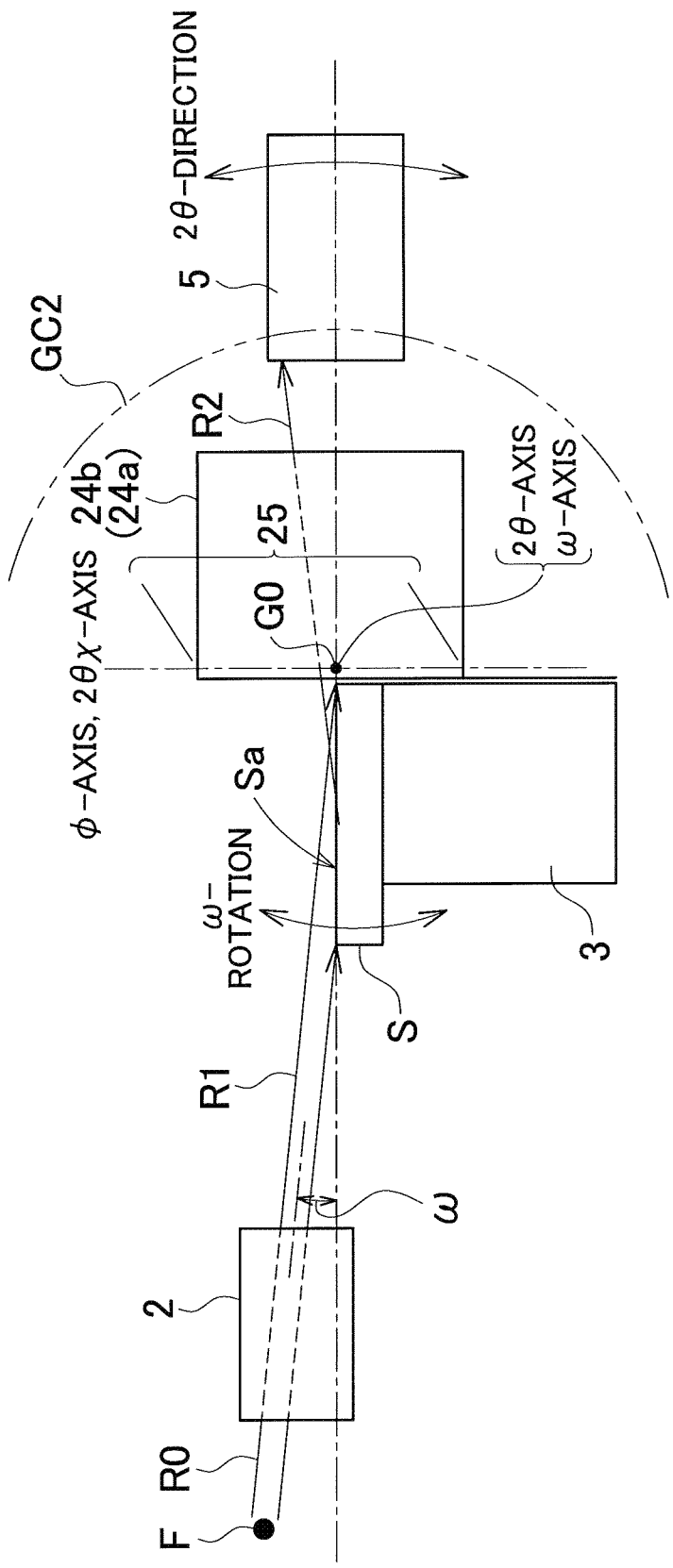
FIG. 7 is a lateral view of the embodiment of FIG. 6.

FIGS. 6 and 7 show another embodiment of the in-plane reciprocal-space mapping apparatus, which is an embodiment of the X-ray diffractometer according to the present invention. FIG. 6 is a plan view of the in-plane reciprocal-space mapping apparatus, and FIG. 7 is a side view of FIG. 6. The same members and devices shown in FIGS. 6 and 7 as the members and devices shown in FIGS. 1 and 2, respectively, will be referred to with the same reference symbols, and a description thereof is omitted.

In the embodiment shown in FIGS. 1 and 2, a pinhole member 4, which is a single flat plate member provided with a pinhole 15 as an X-ray passage port, was used as an X-ray shield member. In contrast, in the embodiment shown in FIGS. 6 and 7, a pair of plate members 24a, 24b in which a long slit 25 in the longitudinal direction is formed as an X-ray passage port is used as the X-ray shield member. The plate members 24a, 24b are disposed in a tapered shape (i.e., a sloped state) as shown in FIG. 6.

In the present embodiment, a slit 25 is formed on the center point G0 of the goniometer circle GC1 (FIG. 6) by the pair of plate members 24a, 24b. Only diffracted X-rays that have passed through the slit 25 are detected by the X-ray detector 5. It is consequently possible to carry out measurement that makes use of angular resolution in the in-plane direction (i.e., the $2\theta_\chi$-direction). More specifically, in-plane reciprocal-space mapping data can be acquired in a short amount of time by repeating several times the step rotation of the sample S about the φ-axis and X-ray exposure in relation to the in-plane direction ($2\theta_\chi$-direction) of the X-ray detector 5.

In the present embodiment, the distance L0 from the center point G0 of the goniometer circles GC1, GC2 to the X-ray-receiving window of the X-ray detector 5 is L0=150 mm, and the X-ray-receiving width W0 of the X-ray detector 5 is W0=77.5 mm. The width W of the slit 25 in the in-plane direction ($2\theta_\chi$-direction) is W=0.5 mm. The X-ray intake angle β formed by the pair of plate members 24a, 24b is β=30°. The X-ray intake angle β is set, as appropriate, in accordance with the X-ray-receiving width W0 of the X-ray detector 5. The specific dimensions can be modified, as appropriate, in accordance with desired measurement conditions.

In the present embodiment, the diffracted X-rays in the in-plane direction ($2\theta_\chi$-direction) are acquired by a single exposure rather than scanning of the X-ray detector. Specifically, $2\theta_\chi$ data for a 30°-angle portion can be acquired in a single exposure. In other words, the mutual overlapping of diffracted X-rays is limited by the slit 25, which is long in the longitudinal direction, and good resolution is obtained.

In the present embodiment, when measurement is carried out in the out-of-plane direction, the diffraction angle along the goniometer circle GC2 in the out-of-plane direction (2θ-direction) in FIG. 7 is measured. In this case, the center point G0 of the goniometer circle GC2 is the same as the center point G0 of the goniometer circle GC1 in the in-plane direction ($2\theta_\chi$-direction) in FIG. 6.

Third Embodiment of the X-Ray Diffractometer

Figure 8:
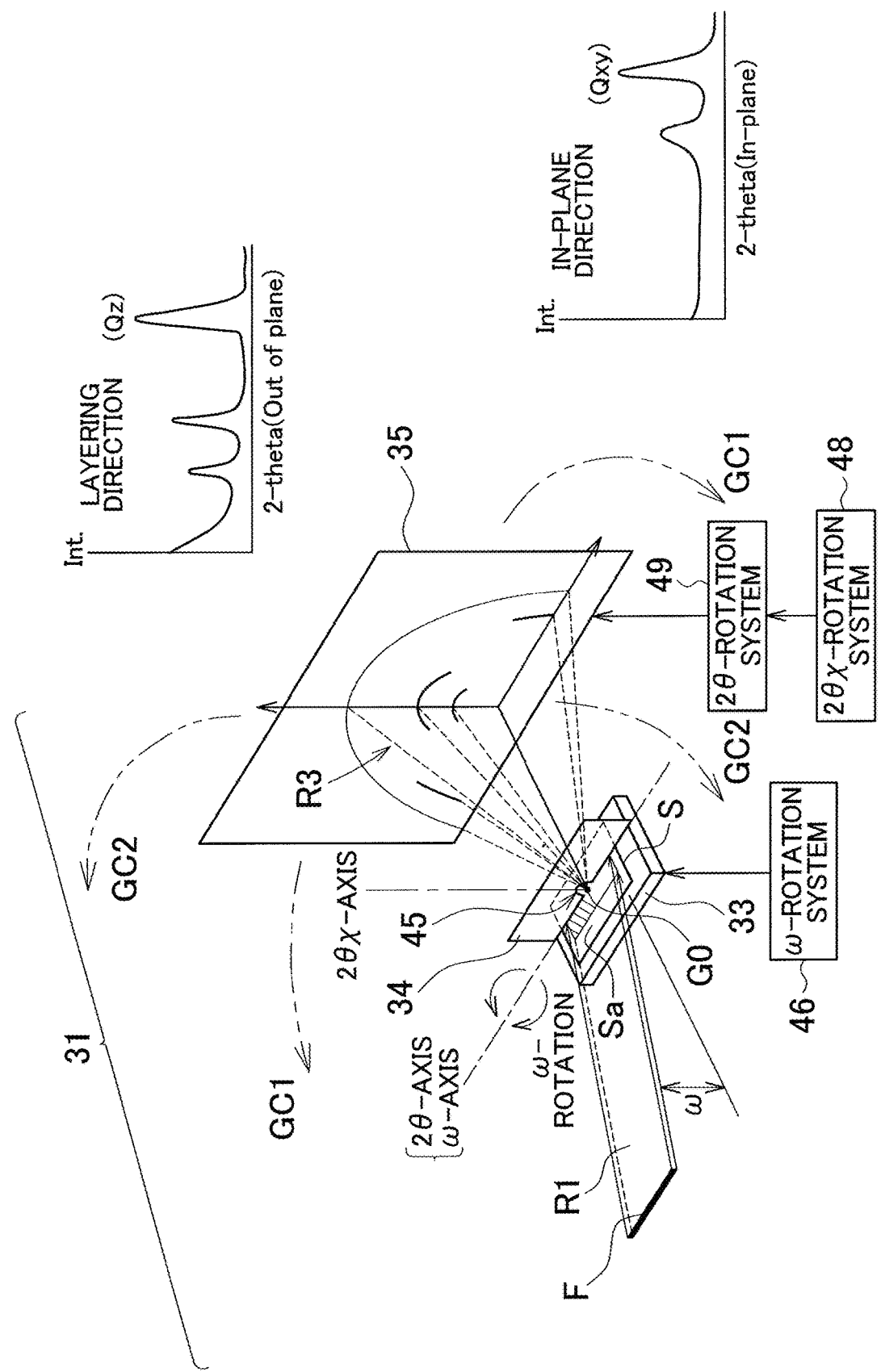
FIG. 8 is a perspective view showing yet another embodiment of the X-ray diffractometer according to the present invention.

FIG. 8 shows an embodiment of the Grazing-Incidence Wide-Angle X-Ray Scattering/Small-Angle X-Ray Scattering Apparatus (GI-WAXS/SAXS Apparatus), which is yet another embodiment of the X-ray diffractometer according to the present invention.

X-ray Small-Angle Scattering is long-known technique for evaluating the nanometer-scale shapes and sizes. Grazing-Incidence Small-Angle X-Ray Scattering (GI-SAXS) is a known technique for causing X-rays to make almost grazing incidence on the surface of a sample and counting the scattered X-rays that almost graze (i.e., at a low angle) and exit the surface of the sample. Furthermore, Grazing-Incidence Wide-Angle X-Ray Scattering (GI-WAXS) is known as a useful measurement technique for causing X-rays to make almost grazing incidence on the surface of a sample and counting the scattered X-rays that exit into a high-angle area with respect to the surface of the sample.

GI-SAXS can be implemented by setting the spacing between the sample and the X-ray detector to be large. On the other hand, GI-WAXS can be implemented by setting the spacing between the sample and the X-ray detector to be small. In the present specification, the term GI-WAXS/SAXS apparatus refers to an apparatus capable of performing both GI-WAXS and GI-SAXS.

A GI-WAXS/SAXS apparatus 31 shown in FIG. 8 has an X-ray source F, a sample stage 33, a pinhole member 34 as an X-ray shield member, and a two-dimensional X-ray detector 35. The X-ray source F is an X-ray source that emits the same line-focus X-rays as the X-ray source F used in the embodiment shown in FIGS. 1 and 2.

The sample S is placed on the sample stage 33. The X-ray source F causes X-rays to be incident on the sample S at a low angle ω of almost grazing the surface Sa of the sample S. An ω-rotation system 46 is connected to the sample stage 33. The ω-rotation system 46 causes the sample stage 33 to rotate (i.e., ω-rotation) about the ω-axis in order to adjust the X-ray incidence angle ω with respect to the sample S. The bottom side of the pinhole member 34 is in contact or close contact with the surface of the sample S. Alternatively, the bottom side of the pinhole member 34 is disposed near the surface of the sample S. A pinhole 45 as an X-ray passage port is provided in substantially the center of the bottom side of the pinhole member 34.

In the present embodiment, the diffraction angle in the in-plane direction is measured about the center point G0 along the goniometer circle GC1 in the in-plane direction. The diffraction angle in the out-of-plane direction is measured about the center point G0 along the goniometer circle GC2 in the out-of-plane direction. The pinhole 45 is disposed on or near the center point G0 of the goniometer circles GC1, GC2.

A $2\theta_\chi$-rotation system 48 and a 2θ-rotation system 49 are provided to the two-dimensional X-ray detector 35. The $2\theta_\chi$-rotation system 48 rotatably moves the two-dimensional X-ray detector 35 along the goniometer circle GC1 about the $2\theta_\chi$-axis extending in the vertical direction of FIG. 8 through the center point G0. The 2θ-rotation system 49 rotatably moves the two-dimensional X-ray detector 35 along the goniometer circle GC2 about the 2θ-axis extending in the horizontal direction of FIG. 8 through the center point G0.

When the desired area of measurement is in the range of the pixel area of the two-dimensional X-ray detector 35, the measurement is carried out with the X-ray detector 35 fixed in place. On the other hand, when the desired area of measurement exceeds the range of the pixel area of the two-dimensional X-ray detector 35, the two-dimensional X-ray detector 35 is rotatably moved along the goniometer circle GC1 or GC2 as required. The pinhole 45 of the pinhole member 34 is disposed on the center point G0 of the goniometer circles GC1 and GC2.

When X-rays are incident on the sample S at a low angle ω almost grazing the surface Sa of the sample S, the X-rays are incident on a wide plane of the sample S indicated by shading, and scattered X-rays exit from this plane almost grazing the surface Sa of the sample S. Among these scattered rays, those that pass through the vicinity of the center point G0 of the goniometer circles GC1, GC2 are selected by the pinhole member 34 and the pinhole 45 and are supplied to the two-dimensional X-ray detector 35. The two-dimensional X-ray detector 35 measure the intensity of the scattered rays in relation to the in-plane direction Qxy of the sample and the normal direction (out-of-plane direction) Qz.

Scattered X-rays or diffracted X-rays are selected by the pinhole 45, and the spreading of the scattered X-rays or diffracted X-rays on the detector that are to be received in the two-dimensional X-ray detector 35 is limited, and the mutual overlapping of scattered X-rays and diffracted X-rays is limited. As a result, an X-ray image is obtained with high resolution on the two-dimensional X-ray detector 35.

Scattered or diffracted X-rays congregate on a wide plane of the sample S indicated by shading and are sent toward the two-dimensional X-ray detector 35. Therefore, the intensity of scattered X-rays and the like received by the two-dimensional X-ray detector 35 is high. Consequently, the X-ray image formed on the two-dimensional X-ray detector 35 is very clear.

In the present embodiment as well, a clear diffracted X-rays image having high resolution can be obtained on the two-dimensional X-ray detector 35 using a very simple configuration in that the pinhole member 34, which is a single plate member, is provided in contact or close contact with the sample S, or the pinhole member 34, which is a single plate member, is disposed near the sample S.

When the degree of preferred orientation of the sample S intensifies, higher-order reflectance (i.e., reflectance in the high-angle area of 2θ or $2\theta_\chi$) may be more difficult to see. This depends on deviation of the measurement orientation expected by the optical system with respect to the actual orientation. In response to this phenomenon, moving the X-ray incidence angle ω toward a higher angle and carrying out measurement at a suitable angle can thereby facilitate viewing of higher-order reflectance, as shown in FIG. 9C. When the X-ray incidence angle ω is moved toward a high angle, it is possible to consider measurement by a common θ/2θ arrangement rather than GI-WAXS/SAXS. Common θ/2θ arrangement is an arrangement state of the optical system in which the angle (2θ) for detecting X-rays exiting the sample using the X-ray detector is measured with the incidence angle (θ) of X-rays in relation to the sample constantly kept at doubled magnitude.

Conventionally, when a two-dimensional X-ray diffraction image is measured, the X-rays incident on the sample must be finely narrowed by a pinhole collimator or the like in order to obtain a clear image of reciprocal lattice points. However, in accordance with the present embodiment, high-angular resolution can be realized by the pinhole 45 and the pinhole member 35, and line-focus X-rays can be used. This is very advantageous in terms of enhancing measurement efficiency.

Example 1

Figure 9A:
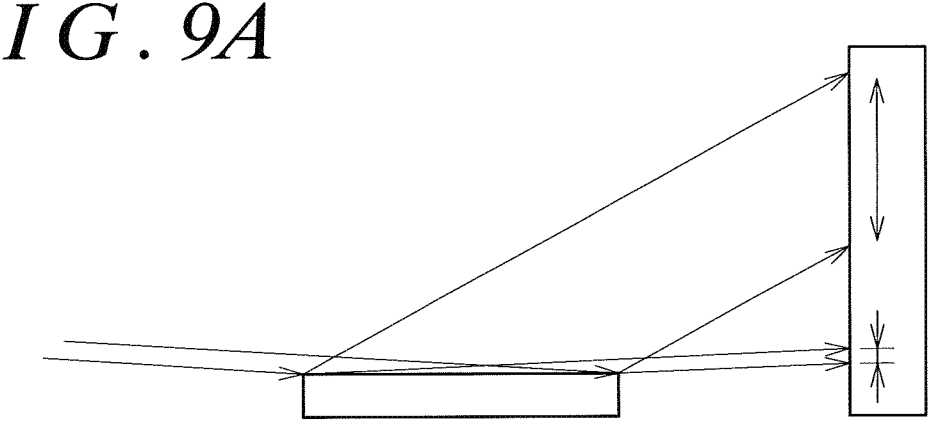
FIGS. 9A, 9B, and 9C are drawings illustrating the functions of the X-ray diffractometer of FIG. 8.
Figure 10:
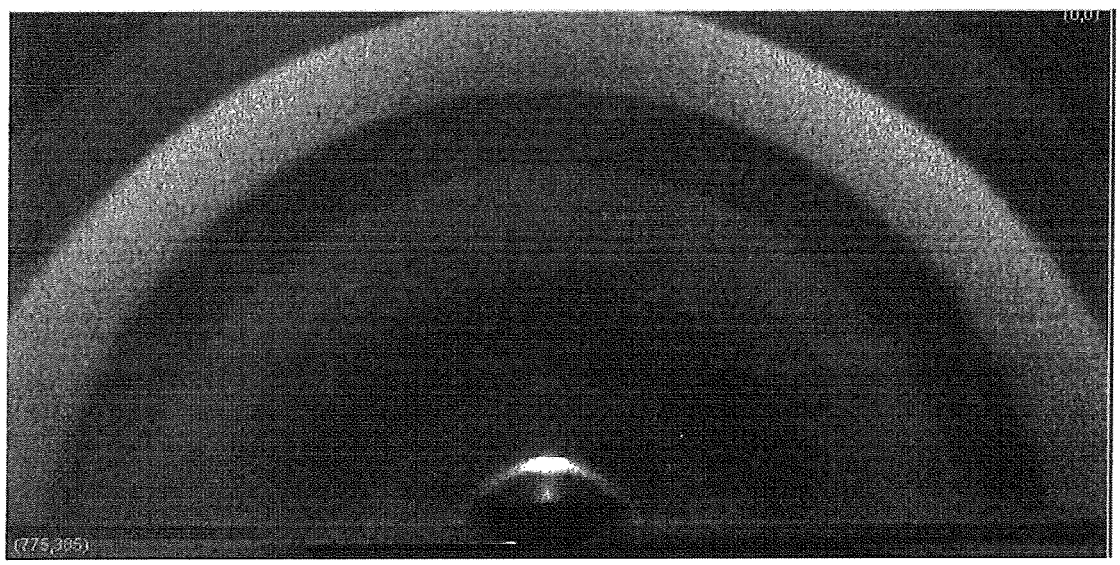
FIG. 10 is a two-dimensional image showing measurement results obtained using the conventional X-ray diffractometer of FIG. 15.
Figure 15:
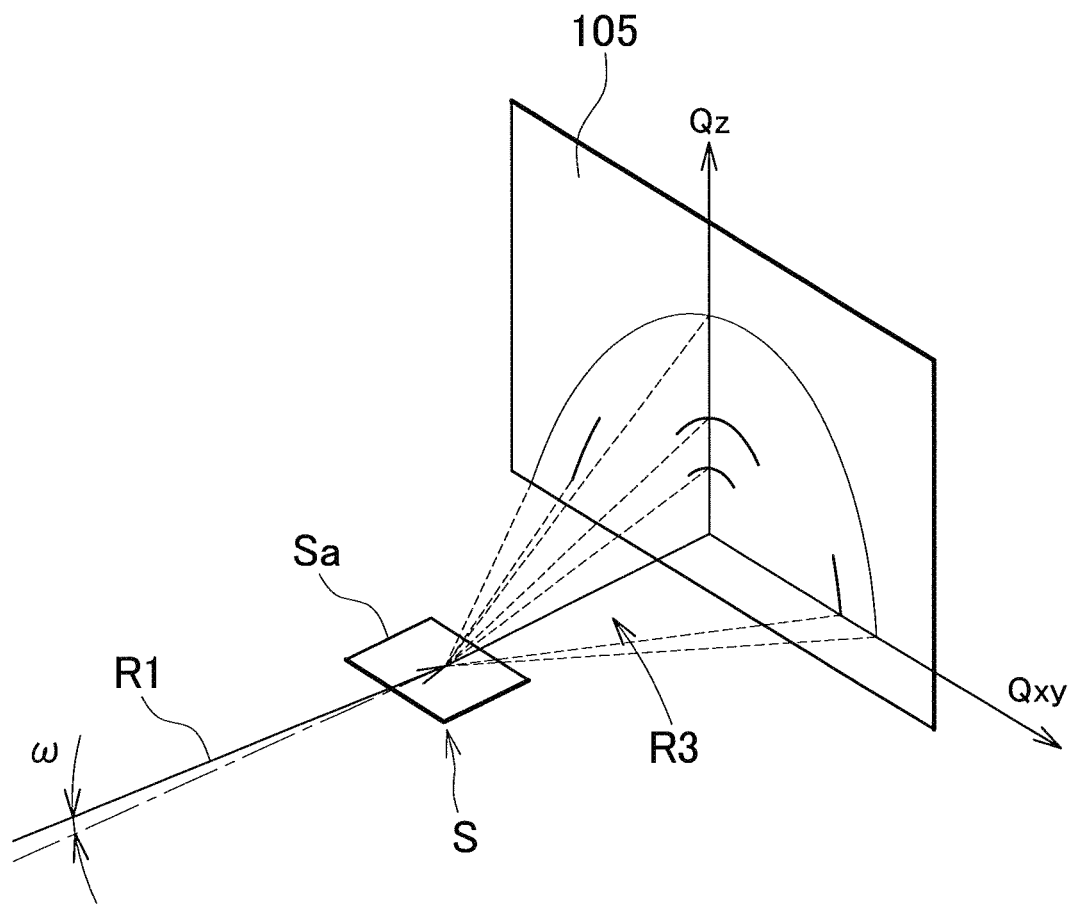
FIG. 15 is a perspective view showing an example of a conventional Grazing-Incidence Wide-Angle X-Ray Scattering/Small-Angle X-ray Scattering (GI-WAXS/SAXS).

In the conventional GI-WAXS apparatus shown in FIG. 15, the X-ray irradiation field on the sample spreads out in accordance with the high-angle area on a two-dimensional image, as shown in FIG. 9A, and the diffracted X-rays therefore spread out. When viewed in a two-dimensional image, this is visible by the spreading of diffracted X-rays in the high-angle area, as shown in FIG. 10.

Figure 9B:
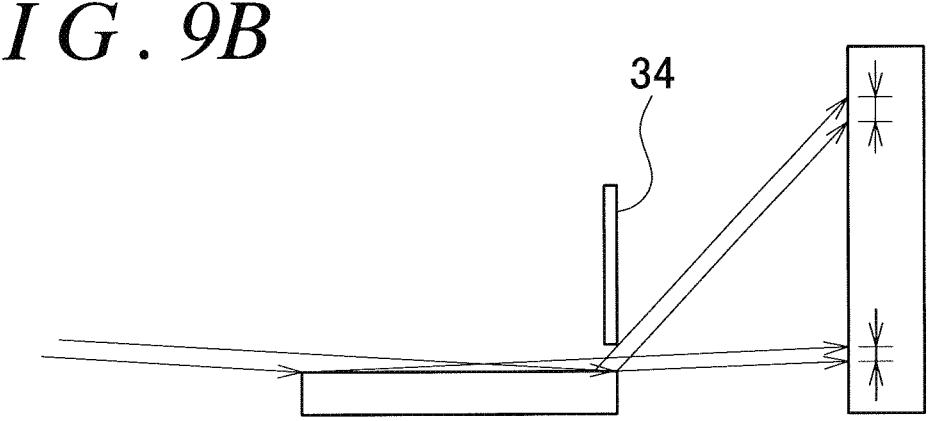
Figure 9C:
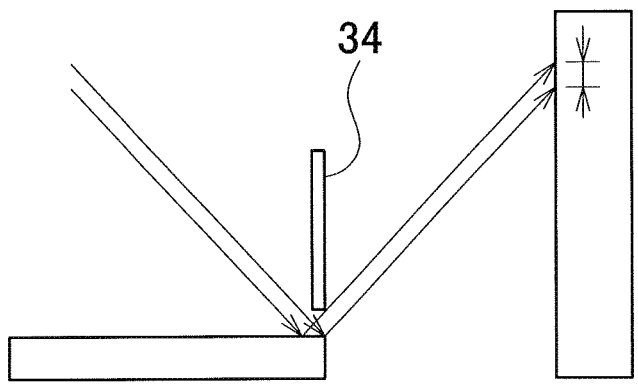

In contrast, in the GI-WAXS/SAXS apparatus of the present embodiment shown in FIG. 8, diffracted X-rays do not spread out even in a high-angle area on the two-dimensional image due to the function of the pinhole member 34, as shown in FIG. 9B. Furthermore, X-rays are irradiated in the shaded wide area of the surface Sa of the sample S in FIG. 8, and high-intensity scattered X-rays can be detected by the X-ray detector 35. For these reasons, it is possible to clearly recognize that higher-order reflectance is obtained when the measurement results of the two-dimensional X-ray detector 35 are seen on a two-dimensional image, as shown in FIG. 11.

Example 2

Figure 12A:
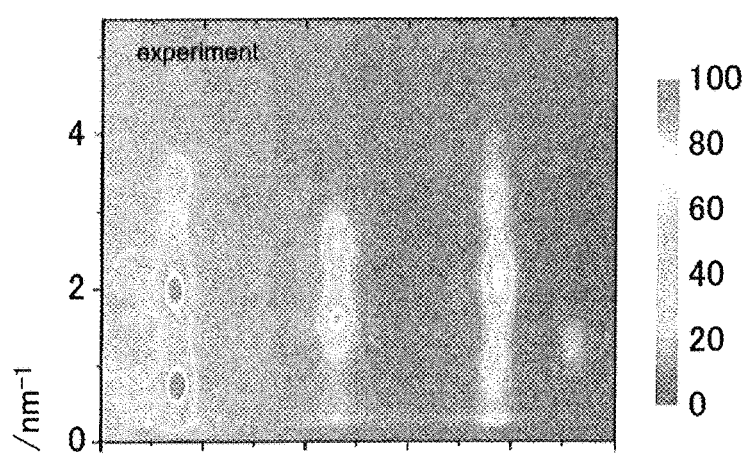
FIGS. 12A, 12B, and 12C are drawings showing a comparison of the measurement results obtained by the X-ray diffractometer according to the present invention in FIG. 8 and the measurement results obtained by a related conventional apparatus.

In the conventional GI-WAXS apparatus of FIG. 15, a pentacene thin film was measured using a scintillation counter, which is a zero-dimensional X-ray detector that lacks resolution, rather than a two-dimensional X-ray detector. In this case, the scintillation counter was caused to scan numerous cycles, and a measurement time of several days was used to perform the measurement. As a result, a two-dimensional image such as shown in FIG. 12A was obtained.

Figure 12B:
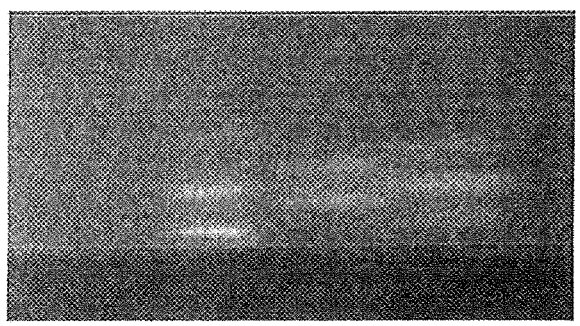

Next, narrowing incident X-rays with a collimator and rather than using pinhole member provided with a pinhole as an opening for forming resolution, as shown in FIG. 15, a GI-WAXS measurement was carried out using the same thin film sample. In this case, measurement was carried out using a camera length of 100 mm and a measurement time of about 30 minutes. As a result, the two-dimensional image shown in FIG. 12B was obtained. In this two-dimensional image, the intensity of scattered X-rays which have exited the sample was low, and the scattered X-rays were not endowed with optimal angular resolution. Therefore, the diffracted X-rays spread out, the diffracted X-rays overlapped each other, and as a result, a clear scattered X-ray image could not be obtained.

Figure 12C:

Next, a GI-WAXS measurement was carried out for the same thin film sample using the GI-WAXS/SAXS apparatus 31 according to the present invention shown in FIG. 8. In this case, the camera length was 65 mm and the measurement time was 30 minutes. As a result, the two-dimensional image shown in FIG. 12C was obtained. In the present example, the spreading of diffracted X-rays and the mutual overlapping of diffracted X-rays are optimally limited by the pinhole member, and therefore the high-resolution data shown in FIG. 12C was obtained. In other words, it was found that widely irradiating the sample with line-focus X-rays to generate high-intensity scattered X-rays, and furthermore imparting optimal angular resolution to the scattered X-rays by the pinhole member 34, as shown in FIG. 8, makes it possible to obtain data, which was conventionally acquired over a very long period of time, in a very short period of time.

OTHER EMBODIMENTS

The present invention was described above using a few preferred embodiments and examples, but the present invention is not limited to those embodiments and the like, and various modifications can be made within the scope of the invention set forth in the claims.

For example, in the embodiments described above, line-focus X-rays are used, but in lieu thereof, it is also possible to use point-focus X-rays.

DESCRIPTION OF SYMBOLS

1: In-plane reciprocal-space mapping apparatus, 2: Incidence-side optical system, 3: Sample stage, 4: Pinhole member (X-ray shield member), 5: X-ray detector, 8: Paraboloidal multilayer mirror, 10: In-plane PSC, 11: Longitudinal limitation slit, 12: Incidence slit, 15: Pinhole (X-ray passage port), 20: Goniometer (angle-measuring device), 24a, 24b: Pair of plate members (X-ray shield member), 25: Slit (X-ray passage port), 31: GI-WAXS/SAX apparatus, 33: Sample stage, 34: Pinhole member (X-ray shield member), 35: Two-dimensional X-ray detector, 45: Pinhole (X-ray passage port), C: Angular scale, F: X-ray source, G0: Goniometer center point, H: Pinhole height, K: Lattice plane, L0: Distance, Qxy: In-plane direction, Qz: Out-of-plane direction, R0: X-rays, R1: Incident X-rays, R2: Diffracted X-rays, R3: Scattered X-rays, S: Sample, Sa: Surface, W: Pinhole width, W0: X-ray-receiving width, α: Incidence angle, β: X-ray intake angle, δ: Sample projection dimension, ω: X-ray incidence angle

The invention claimed is:

1. An X-ray diffractometer for obtaining X-ray diffraction angles of diffracted X-rays, comprising:
    an x-ray source configured to emit x-rays at a sample;
    an X-ray detector configured to detect diffracted X-rays diffracted at the sample angles about a center point of goniometer circles when x-rays are emitted at the sample; and
    an X-ray shield member provided with an X-ray passage port that is maintained on a center point of said goniometer circles,
    wherein
        the X-rays diffracted at the sample so as to pass through the center point of the goniometer circles pass through the X-ray passage port, and
        the X-rays diffracted at the sample so as to pass through areas other than the center point of the goniometer circles are shielded by the X-ray shield member.

2. The X-ray diffractometer according to claim 1, wherein the X-ray shield member is disposed in contact with the surface of the sample or near the surface of the sample.

3. The X-ray diffractometer according to claim 1, wherein the X-ray shield member is disposed in contact with the end face of the sample on the X-ray detector side, or near the end face of the sample on the X-ray detector side.

4. The X-ray diffractometer according to claim 1, wherein the X-ray passage port is a pinhole extending in the direction intersecting the sample, or a slit extending in the direction intersecting the sample.

5. The X-ray diffractometer according to claim 1, wherein the X-rays incident on the sample are line-focus X-rays, and the lengthwise direction of the line focus is the direction parallel to the surface of the sample.

6. The X-ray diffractometer according to claim 1, wherein X-rays are caused to be incident at a low angle with respect to the sample so that diffraction occurs on a lattice plane perpendicular to the surface of the sample.

7. The X-ray diffractometer according to claim 6, further comprising:
    an ω-rotation system for adjusting the incidence angle of X-rays on the sample;
    a φ-rotation system for rotating the sample in-plane;
    a 2θ-rotation system for moving the X-ray detector in the out-of-plane direction; and
    a $2\theta_\chi$-rotation system for moving the X-ray detector in the in-plane direction;
    wherein the ω-rotation system, the φ-rotation system, the 2θ-rotation system, and the $2\theta_\chi$-rotation system operate about the center point, as an origin, of the goniometer circles, which is a shared center point.

* * * * *